(12) United States Patent
Selim et al.

(10) Patent No.: US 11,295,136 B2
(45) Date of Patent: *Apr. 5, 2022

(54) PREDICTIVE DATA ANALYSIS USING IMAGE REPRESENTATIONS OF CATEGORICAL AND SCALAR FEATURE DATA

(71) Applicant: Optum Services (Ireland) Limited, Dublin (IE)

(72) Inventors: Ahmed Selim, Dublin (IE); Michael Bridges, Dublin (IE)

(73) Assignee: Optum Services (Ireland) Limited, Dublin (IE)

(*) Notice: Subject to any disclaimer, the term of this patent is extended or adjusted under 35 U.S.C. 154(b) by 225 days.

This patent is subject to a terminal disclaimer.

(21) Appl. No.: 16/670,546

(22) Filed: Oct. 31, 2019

(65) Prior Publication Data

US 2021/0133455 A1   May 6, 2021

(51) Int. Cl.
| | |
|---|---|
| *G06K 9/00* | (2006.01) |
| *G06K 9/32* | (2006.01) |
| *G16H 30/40* | (2018.01) |
| *G06N 3/08* | (2006.01) |
| *G06N 20/00* | (2019.01) |

(52) U.S. Cl.
CPC ......... *G06K 9/00684* (2013.01); *G06K 9/325* (2013.01); *G06N 3/08* (2013.01); *G06N 20/00* (2019.01); *G16H 30/40* (2018.01)

(58) Field of Classification Search
CPC .... G06K 9/00684; G06K 9/325; G06N 20/00; G06N 3/08; G06N 5/04; G16H 30/40; G16H 50/20; G16H 50/70; G16H 30/20; G16H 40/20; G06T 11/00;
(Continued)

(56) References Cited

U.S. PATENT DOCUMENTS

| | | |
|---|---|---|
| 9,342,579 B2 | 5/2016 | Cao et al. |
| 10,223,501 B1 | 3/2019 | Schneider et al. |

(Continued)

OTHER PUBLICATIONS

Final Office Action for U.S. Appl. No. 16/670,504, dated Jul. 26, 2021, (28 pages), United States Patent and Trademark Office, USA.
(Continued)

*Primary Examiner* — Xin Jia
(74) *Attorney, Agent, or Firm* — Alston & Bird LLP

(57) ABSTRACT

There is a need for more effective and efficient predictive data analysis solutions and/or more effective and efficient solutions for generating image representations of categorical/scalar data. Various embodiments of the present invention address one or more of the noted technical challenges. In one example, a method comprises receiving the one or more categorical input features; generating an image representation of the one or more categorical input features, wherein the image representation comprises image region values each associated with a categorical input feature, and further wherein each image region value of the one or more image region values is determined based at least in part on the corresponding categorical input feature associated with the image region value; and processing the image representation using an image-based machine learning model to generate the image-based predictions.

20 Claims, 25 Drawing Sheets

(58) Field of Classification Search
CPC ....... G06T 2207/20081; G06T 2210/41; G06T 7/0012; G06T 2207/20084
See application file for complete search history.

(56) References Cited

U.S. PATENT DOCUMENTS

| | | | |
|---|---|---|---|
| 10,891,352 | B1 | 1/2021 | Hane et al. |
| 2015/0065803 | A1* | 3/2015 | Douglas ............. A61B 1/00045 600/200 |
| 2015/0297172 | A1 | 10/2015 | Takagi et al. |
| 2016/0055427 | A1 | 2/2016 | Adjaoute |
| 2016/0364862 | A1 | 12/2016 | Reicher et al. |
| 2017/0091401 | A1 | 3/2017 | Kemp |
| 2017/0178321 | A1 | 6/2017 | Nieves et al. |
| 2017/0308981 | A1 | 10/2017 | Razavian et al. |
| 2018/0268320 | A1 | 9/2018 | Shekhar |
| 2018/0315507 | A1 | 11/2018 | Mortazavi et al. |
| 2018/0330808 | A1 | 11/2018 | Xie et al. |
| 2019/0005410 | A1 | 1/2019 | Shekhar et al. |
| 2019/0080416 | A1 | 3/2019 | Smith et al. |
| 2019/0295228 | A1 | 9/2019 | Liu et al. |
| 2020/0034366 | A1 | 1/2020 | Kivatinos et al. |
| 2020/0151444 | A1* | 5/2020 | Price .................... G06K 9/6277 |
| 2020/0320139 | A1 | 10/2020 | Duishoev et al. |
| 2020/0381090 | A1 | 12/2020 | Apostolova et al. |
| 2021/0027194 | A1 | 1/2021 | Monaghan et al. |
| 2021/0133959 | A1 | 5/2021 | Selim et al. |
| 2021/0134438 | A1 | 5/2021 | Selim et al. |
| 2021/0134439 | A1 | 5/2021 | Selim et al. |

OTHER PUBLICATIONS

NonFinal Office Action for U.S. Appl. No. 16/670,504, filed Mar. 9, 2021, (19 pages), United States Patent and Trademark Office, USA.
Guo, Cheng et al. Entity Embeddings of Categorical Variables, arXiv preprint arXiv:1604.06737v1, Apr. 22, 2016, (9 pages).
NonFinal Office Acton for U.S. Appl. No. 16/670,615, dated Jun. 16, 2021, (28 pages), United States Patent and Trademark Office, USA.
Cai, Xiangrui et al. "Medical Concept Embedding With Time-Aware Attention," arXiv preprint arXiv: 1806.02873v1, Jun. 6, 2018, (7 pages).
Choi, Edward et al. "MiME: Multilevel Medical Embedding of Electronic Health Records For Predictive Healthcare," arXiv preprint arXiv: 1810.09593v1, Oct. 22, 2018, (17 pages).
Geng, Yujuan et al. Patient Outcome Prediction Via Convolutional Neural Networks Based On Multi-Granularity Medical Concept Embedding, 2017 IEEE International Conference On Bioinformatics and Biomedicine (BIBM), Nov. 13-16, 2017, pp. 770-777,, Kansas City, MO, USA. DOI: 10.1109/BIBM.2017.8217753.
Landi, Isotta et al. "Deep Representation Learning of Electronic Health Records To Unlock Patient Stratification At Scale," NPJ|Digital Medicine, vol. 3, No. 1, pp. 1-11, Jul. 17, 2020.
Final Office Action for U.S. Appl. No. 16/670,615, dated Oct. 18, 2021, (31 pages), United States Patent and Trademark Office, USA.
Notice of Allowance and Fee(s) Due for U.S. Appl. No. 16/670,504, dated Oct. 18, 2021, (11 pages), United States Patent and Trademark Office, USA.

* cited by examiner

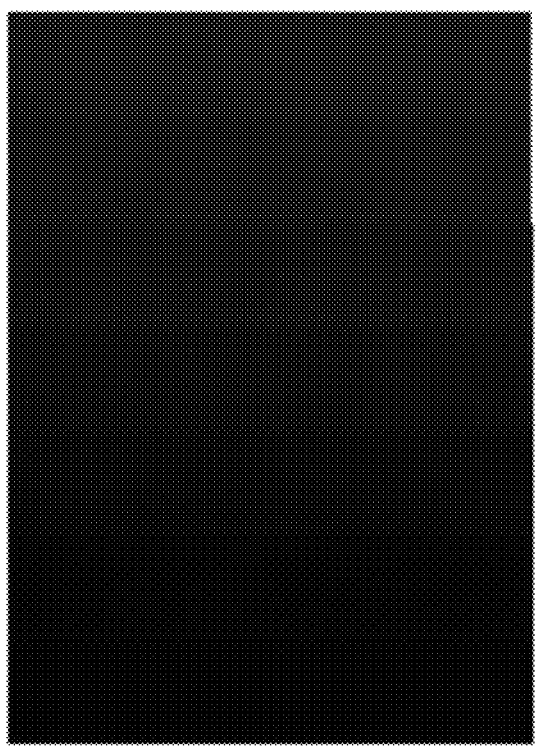
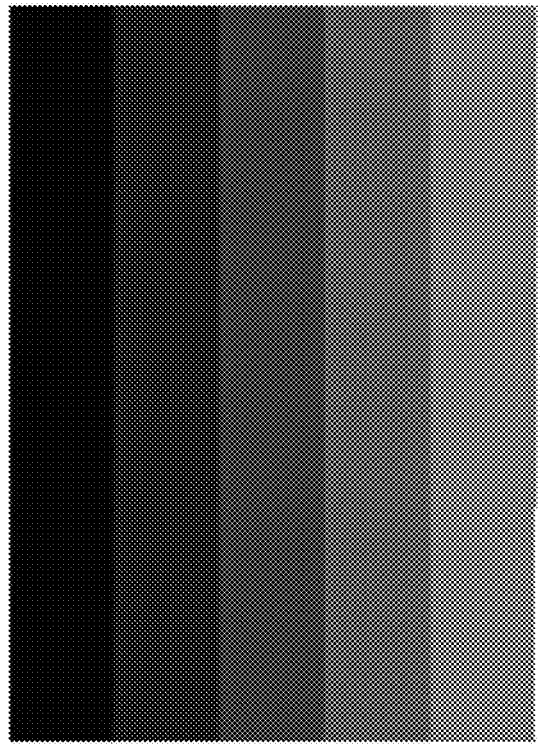
FIG. 9A
FIG. 9B

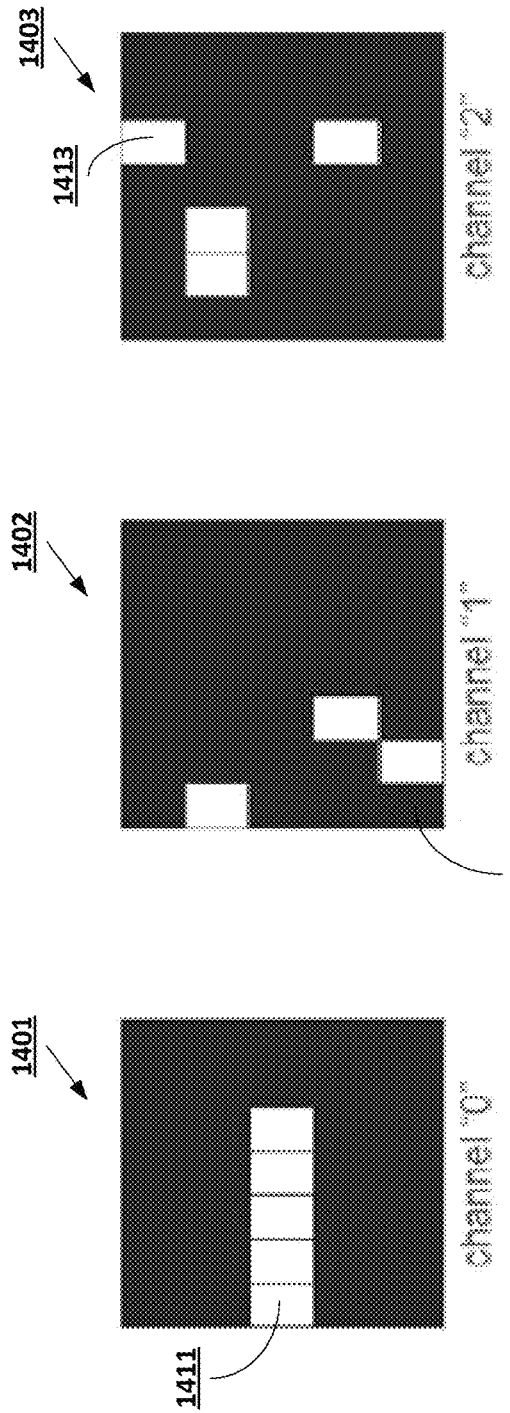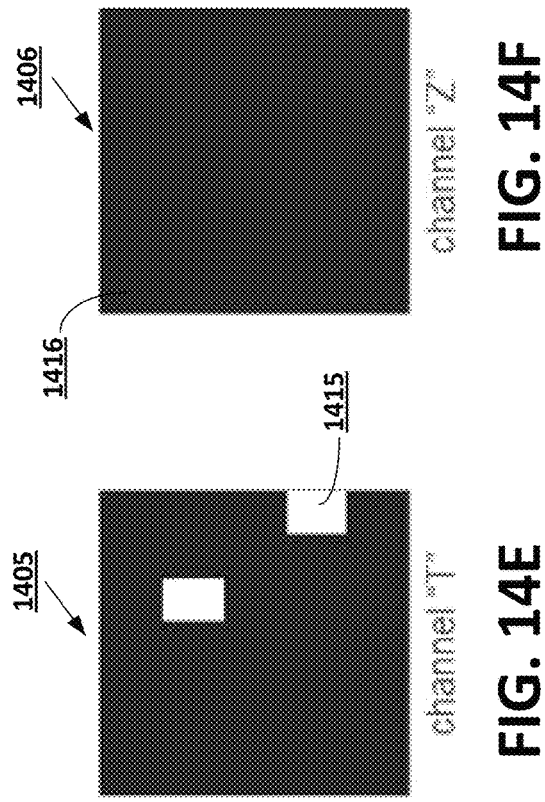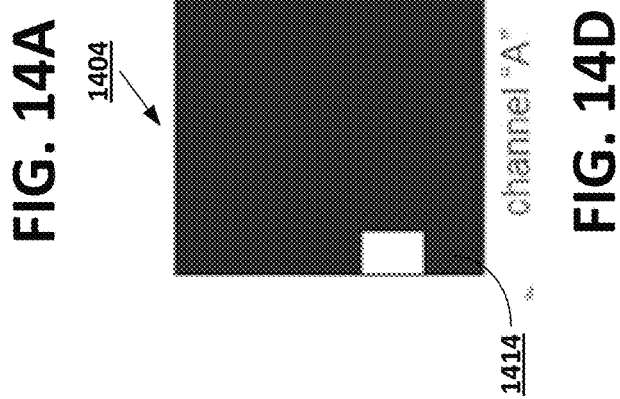

PREDICTIVE DATA ANALYSIS USING IMAGE REPRESENTATIONS OF CATEGORICAL AND SCALAR FEATURE DATA

BACKGROUND

The present invention addresses technical challenges related to performing predictive data analysis in a computationally efficient and predictively reliable manner. Existing predictive data analysis systems are ill-suited to efficiently and reliably performing predictive data analysis in various domains, such as domains that are associated with high-dimensional categorical feature spaces with a high degree of cardinality.

BRIEF SUMMARY

In general, embodiments of the present invention provide methods, apparatus, systems, computing devices, computing entities, and/or the like for predictive data analysis of categorical data using image transformations. Certain embodiments utilize systems, methods, and computer program products that perform predictive analysis of features using image transformations (e.g., reserved-spatial-location image transformations, reserved-pattern-based image transformations, coordinate-based reserved-spatial-location image transformations, feature-based reserved-spatial-location image transformations, and scalar reserved-spatial-location image transformation).

In accordance with one aspect, a method is provided. In one embodiment, the method comprises: determining an image region value corresponding to each categorical input feature of the one or more categorical input features, wherein at least one image region value of the one or more image region values is configured to depict a visual representation of textual data associated with the corresponding categorical input feature that is associated with the at least one image region value; and generating the image representation based on each image region value corresponding to a categorical input feature of the one or more categorical input features.

In accordance with another aspect, a computer program product is provided. The computer program product may comprise at least one computer-readable storage medium having computer-readable program code portions stored therein, the computer-readable program code portions comprising executable portions configured to: determine an image region value corresponding to each categorical input feature of the one or more categorical input features, wherein at least one image region value of the one or more image region values is configured to depict a visual representation of textual data associated with the corresponding categorical input feature that is associated with the at least one image region value; and generate the image representation based on each image region value corresponding to a categorical input feature of the one or more categorical input features.

In accordance with yet another aspect, an apparatus comprising at least one processor and at least one memory including computer program code is provided. In one embodiment, the at least one memory and the computer program code may be configured to, with the processor, cause the apparatus to: determine an image region value corresponding to each categorical input feature of the one or more categorical input features, wherein at least one image region value of the one or more image region values is configured to depict a visual representation of textual data associated with the corresponding categorical input feature that is associated with the at least one image region value; and generate the image representation based on each image region value corresponding to a categorical input feature of the one or more categorical input features.

BRIEF DESCRIPTION OF THE DRAWINGS

Figure 1:
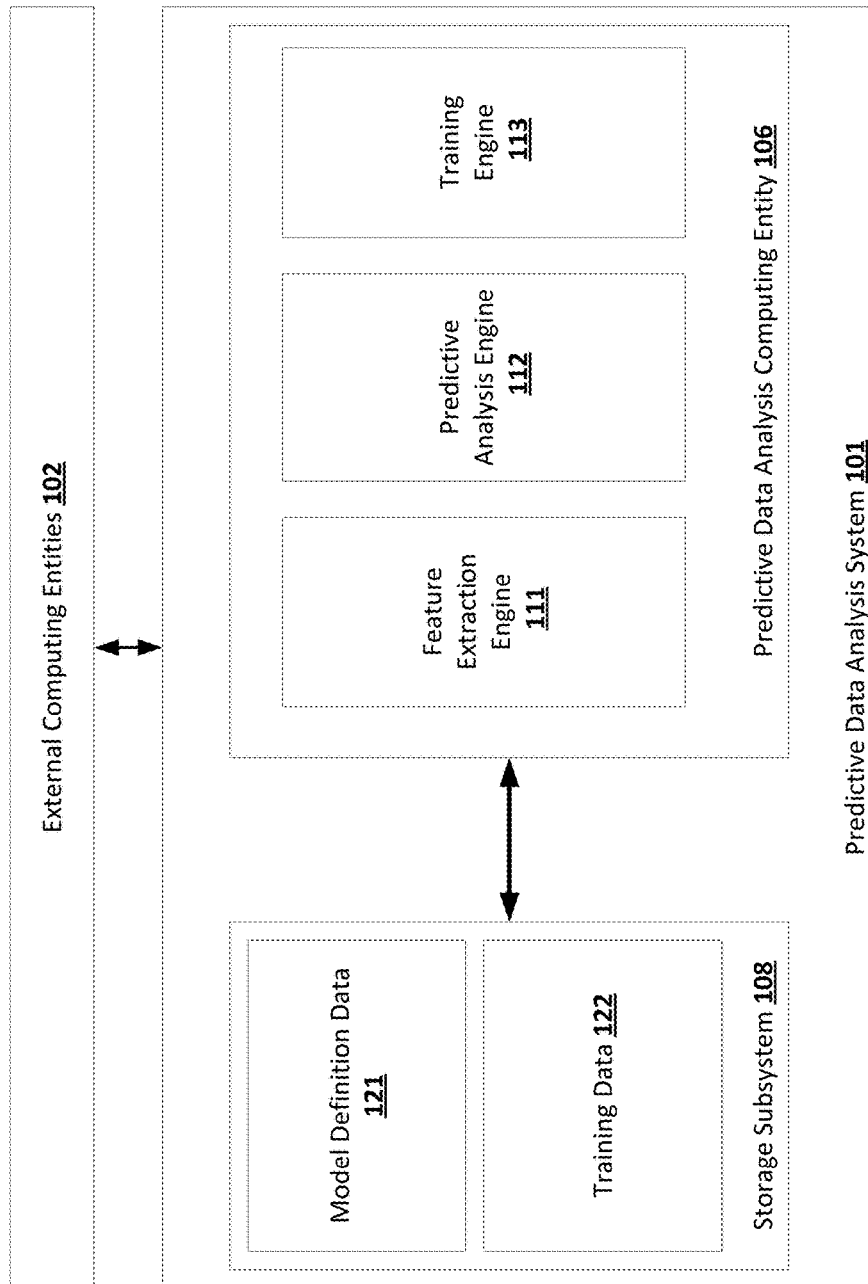

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
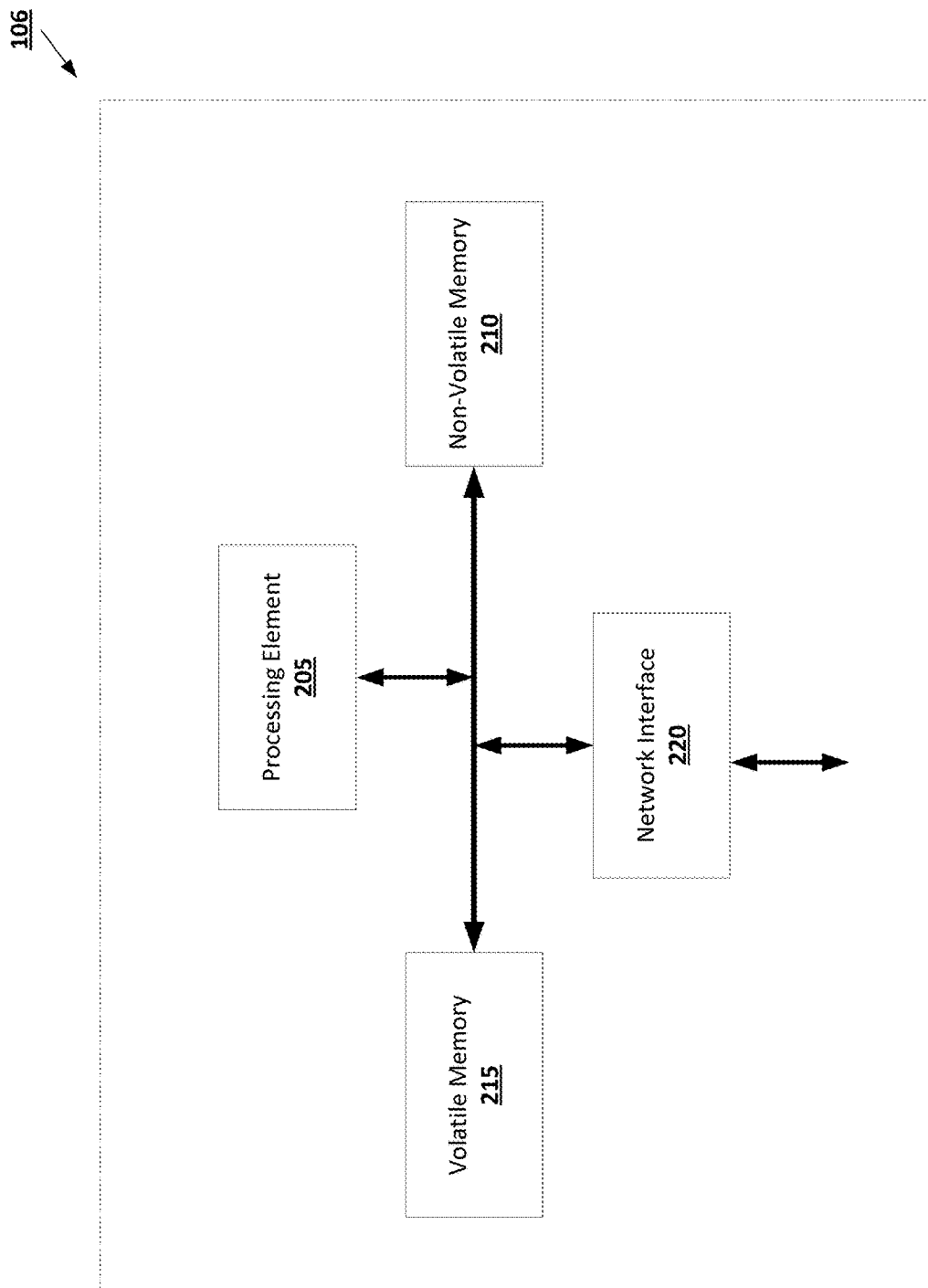

FIG. 2 provides an example predictive data analysis computing entity in accordance with some embodiments discussed herein.

Figure 3:
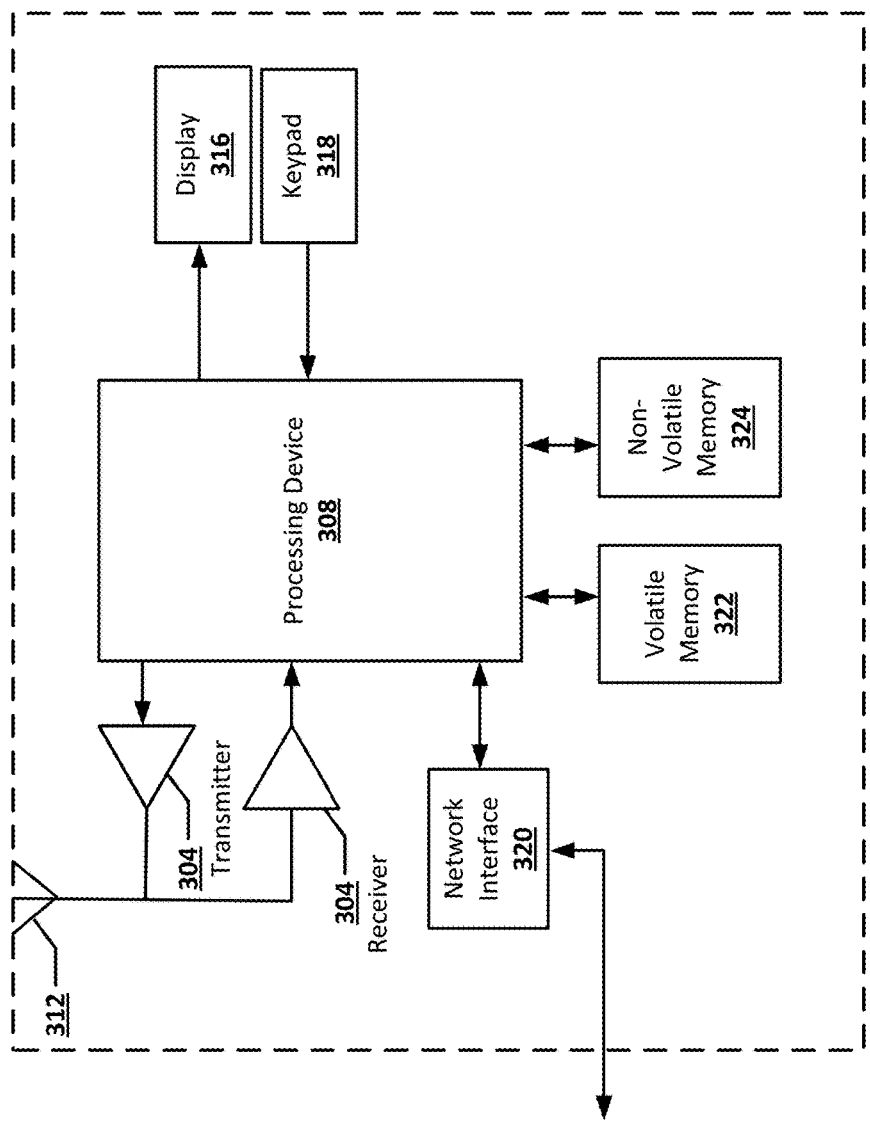

FIG. 3 provides an example external computing entity in accordance with some embodiments discussed herein.

Figure 4:
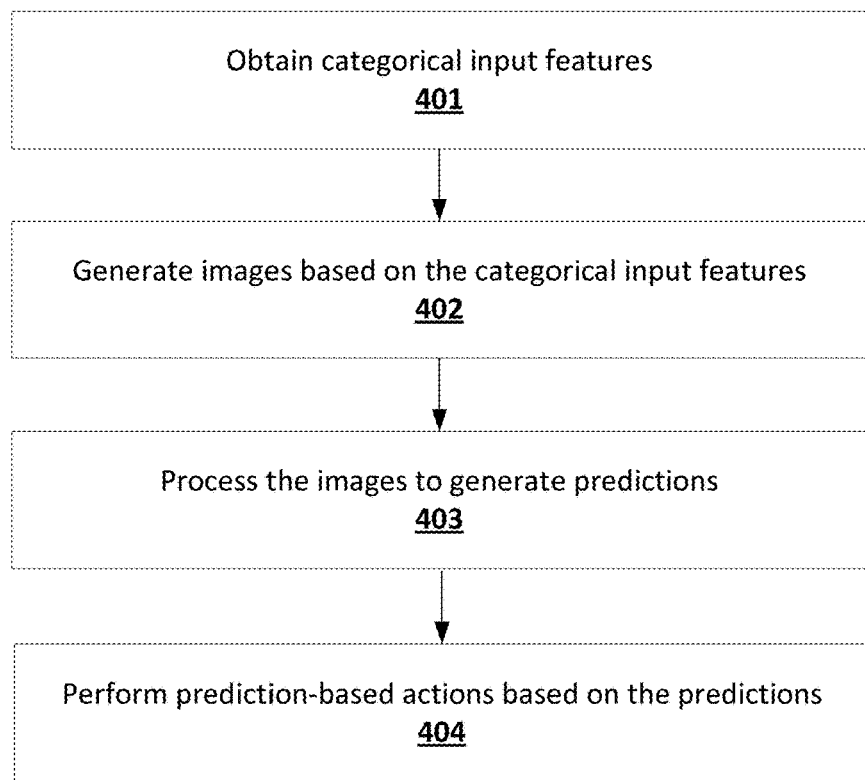

FIG. 4 is a flowchart diagram of an example process for performing image-based predictive data analysis in accordance with some embodiments discussed herein.

Figure 5:
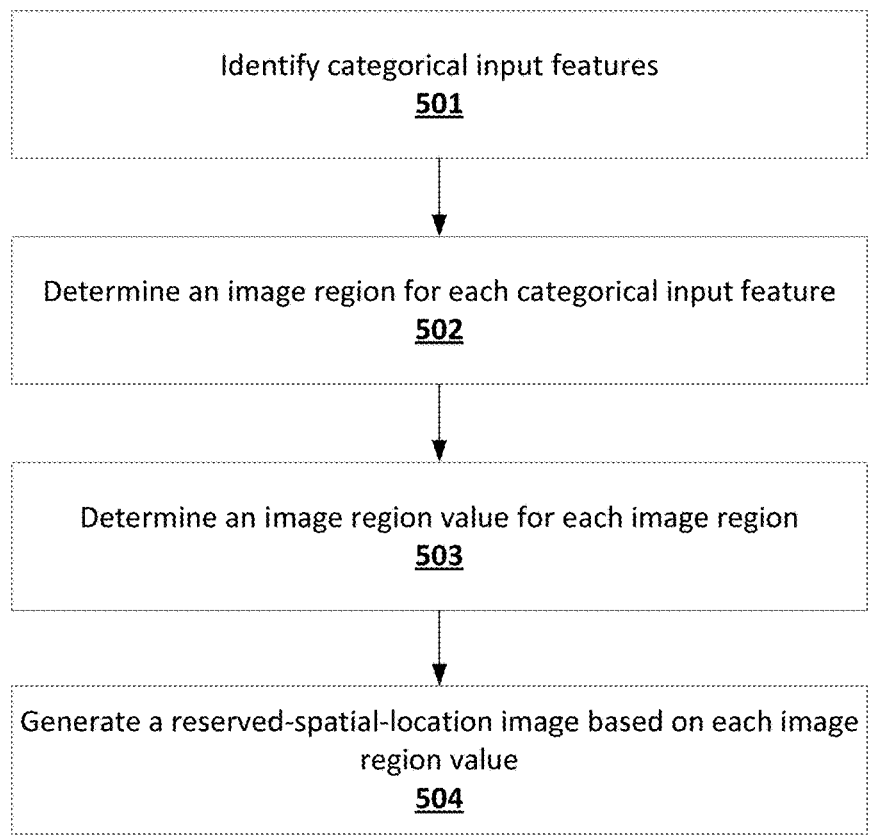

FIG. 5 is a flowchart diagram of an example process for performing reserved-spatial-location image transformation in accordance with some embodiments discussed herein.

Figure 6:
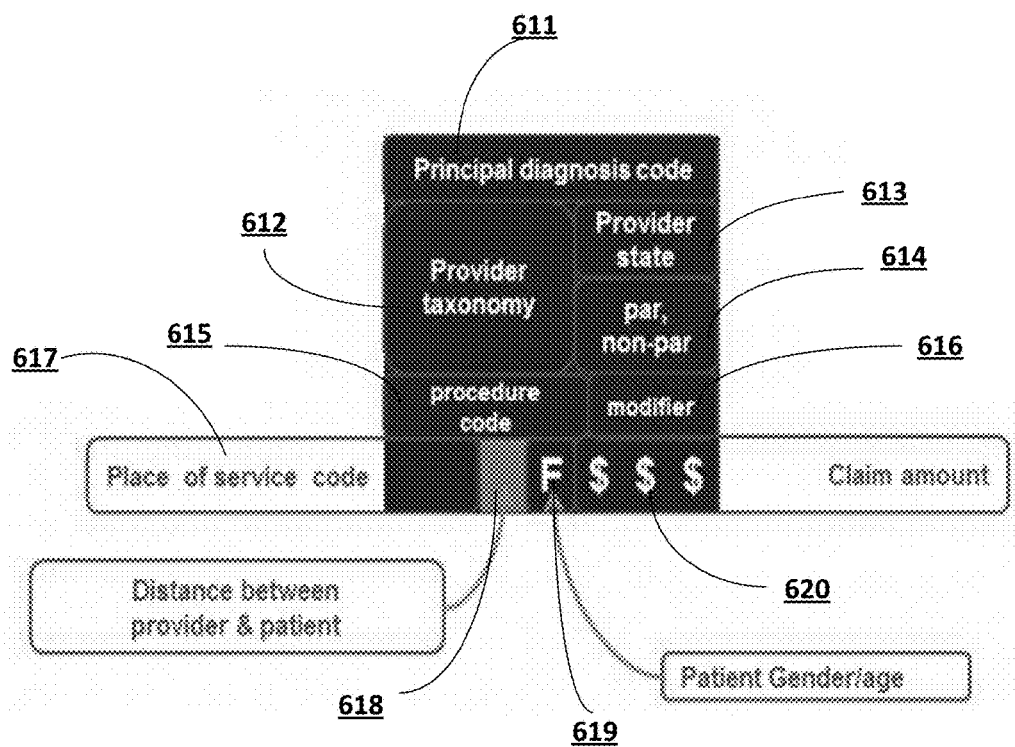

FIG. 6 provides an operational example of a reserved-spatial-location division of an image space into various image regions in accordance with some embodiments discussed herein.

Figure 7:
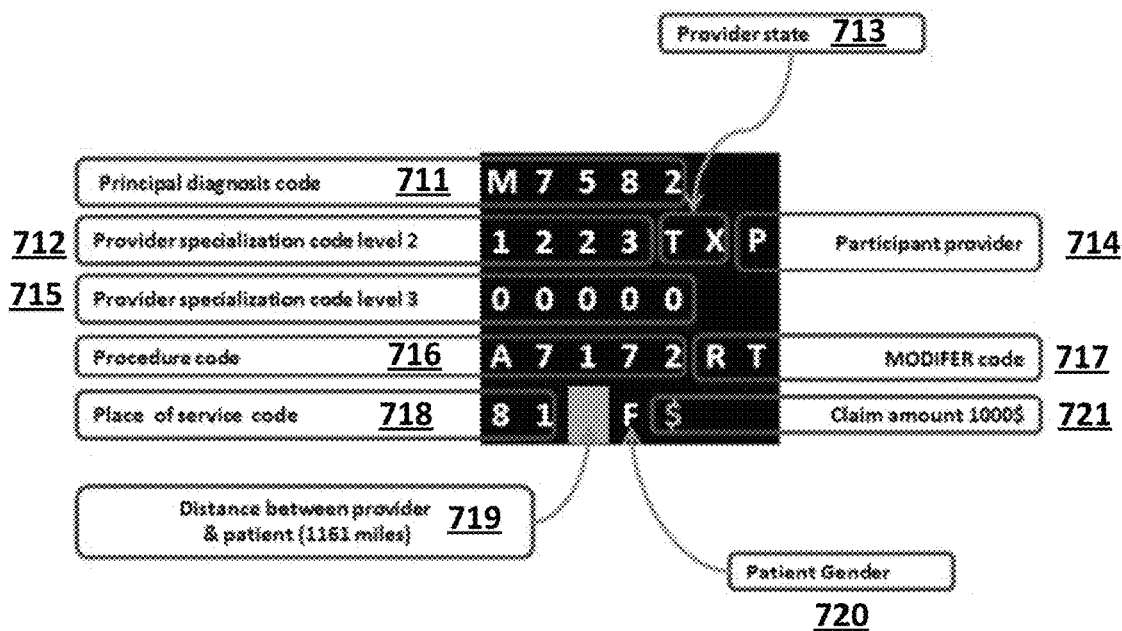

FIG. 7 provides an operational example of a reserved-spatial-location image in accordance with some embodiments discussed herein.

Figure 8:
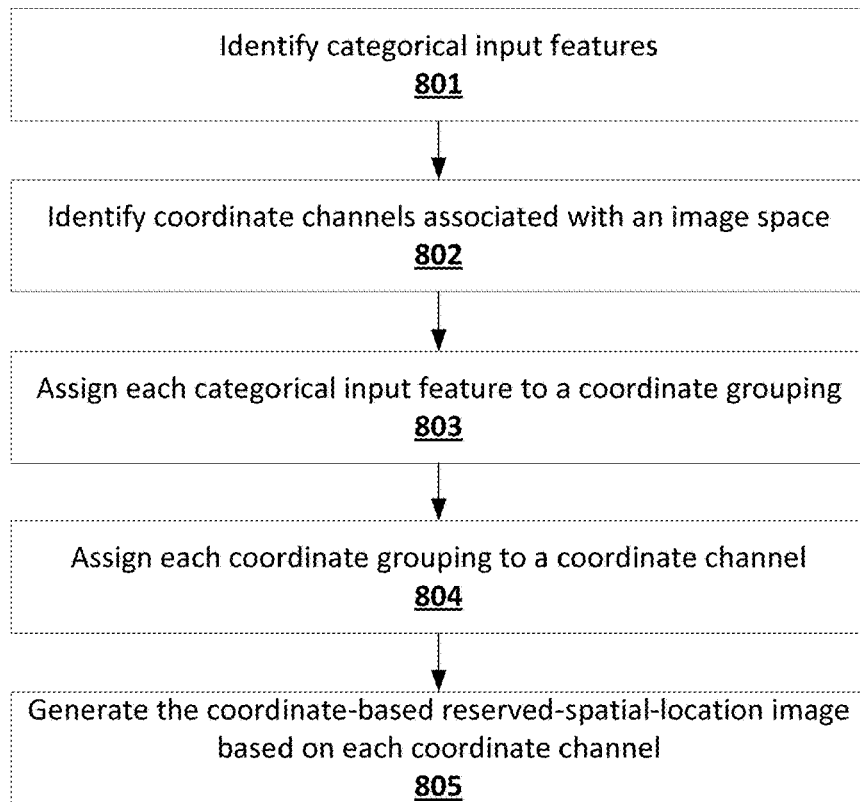

FIG. 8 is a flowchart diagram of an example process for performing coordinate-based reserved-spatial-location image transformation in accordance with some embodiments discussed herein.

Figure 9C:
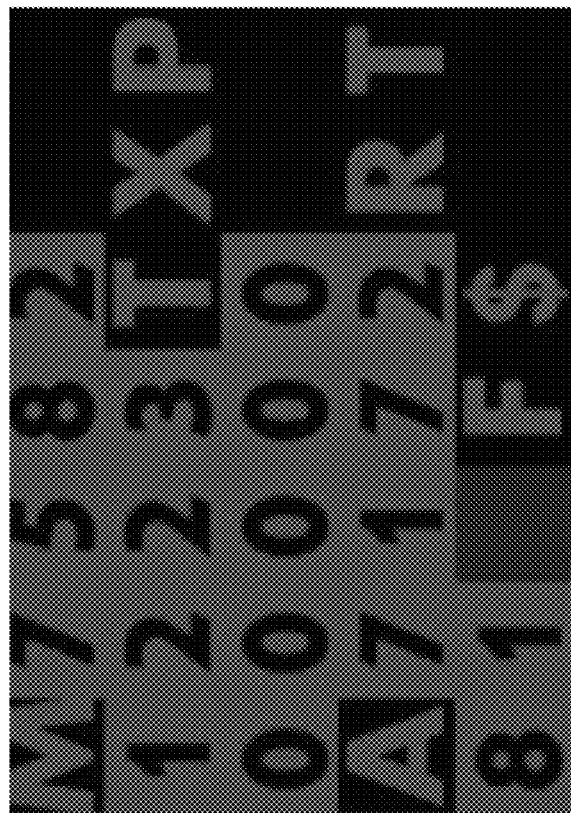

FIGS. 9A-9C provide operational examples of color-based channels in accordance with some embodiments discussed herein.

Figure 10:
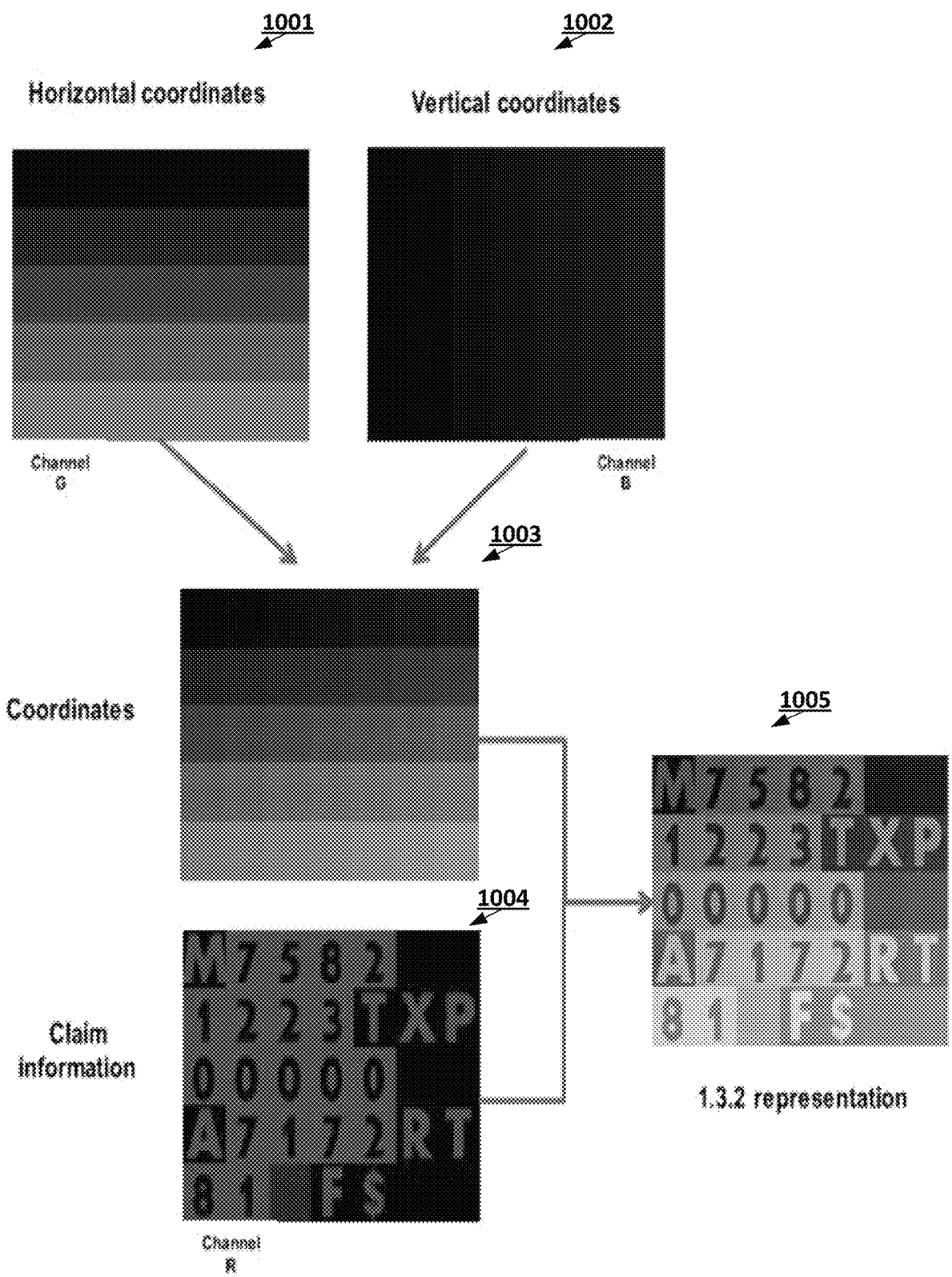

FIG. 10 provides an operational example of generating a coordinate-based reserved-spatial-location image in accordance with some embodiments discussed herein.

Figure 11:
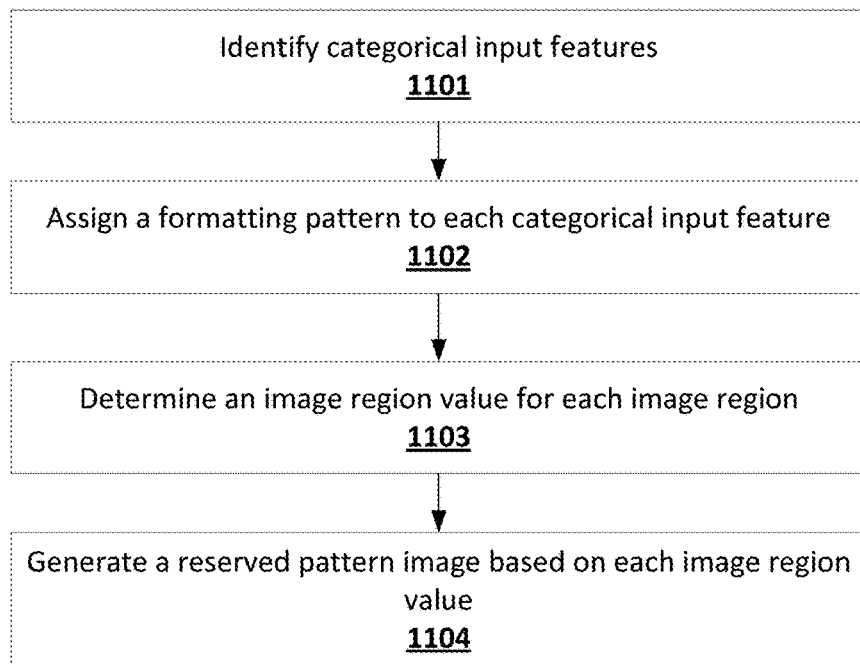

FIG. 11 is a flowchart diagram of an example process for performing reserved-pattern-based image transformation in accordance with some embodiments discussed herein.

Figure 12:
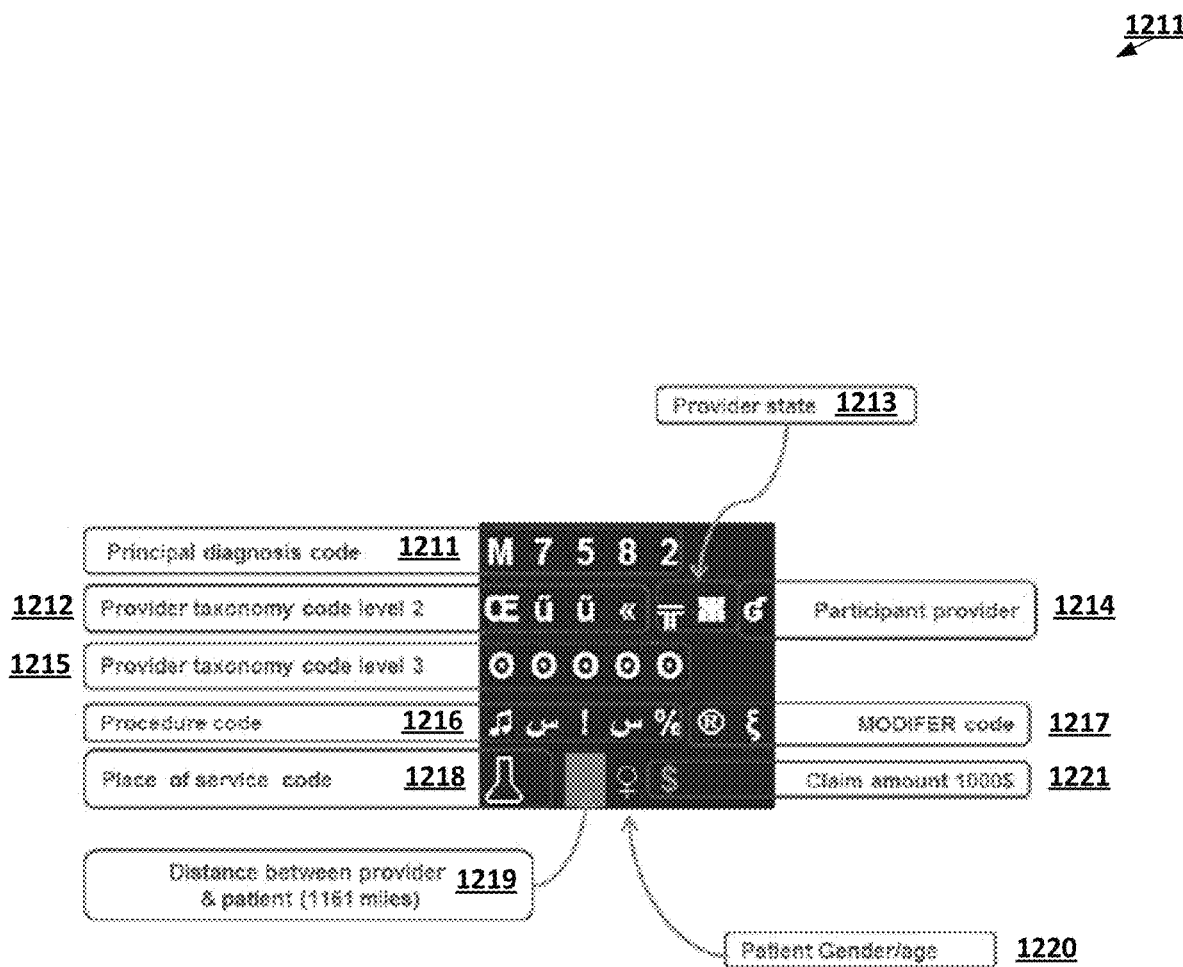

FIG. 12 provides an operational example of a reserved-pattern image in accordance with some embodiments discussed herein.

Figure 13:
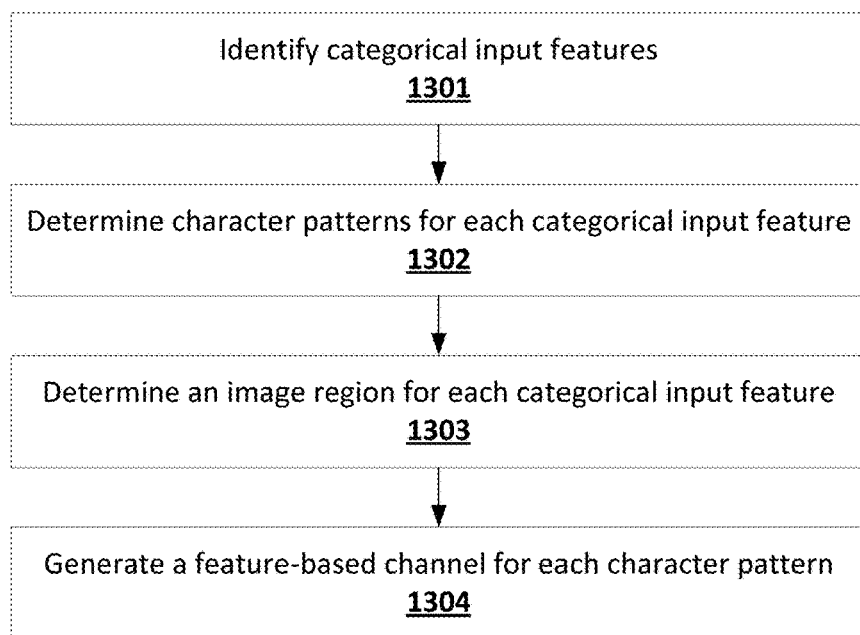

FIG. 13 is a flowchart diagram of an example process for performing feature-based reserved-spatial-location image transformation in accordance with some embodiments discussed herein.

FIGS. 14A-14F provide operational examples of feature-based channels in accordance with some embodiments discussed herein.

Figure 15:
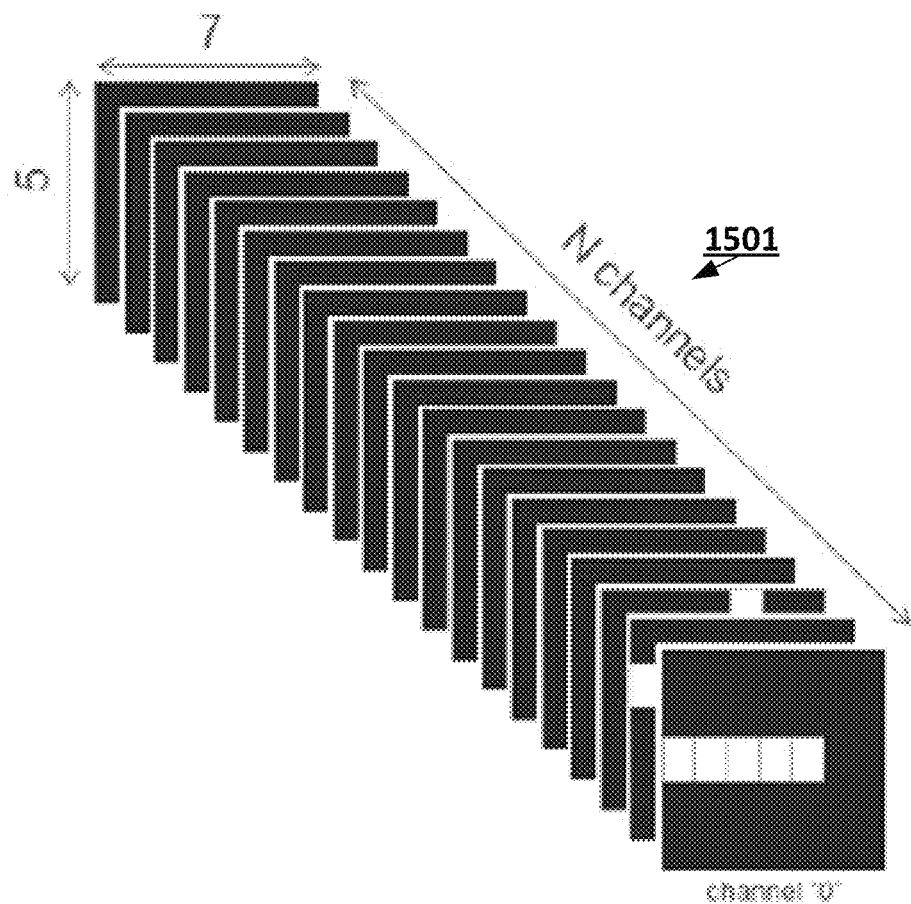

FIG. 15 provides an operational example of a set of feature-based channels for a set of categorical input features in accordance with some embodiments discussed herein.

Figure 16:
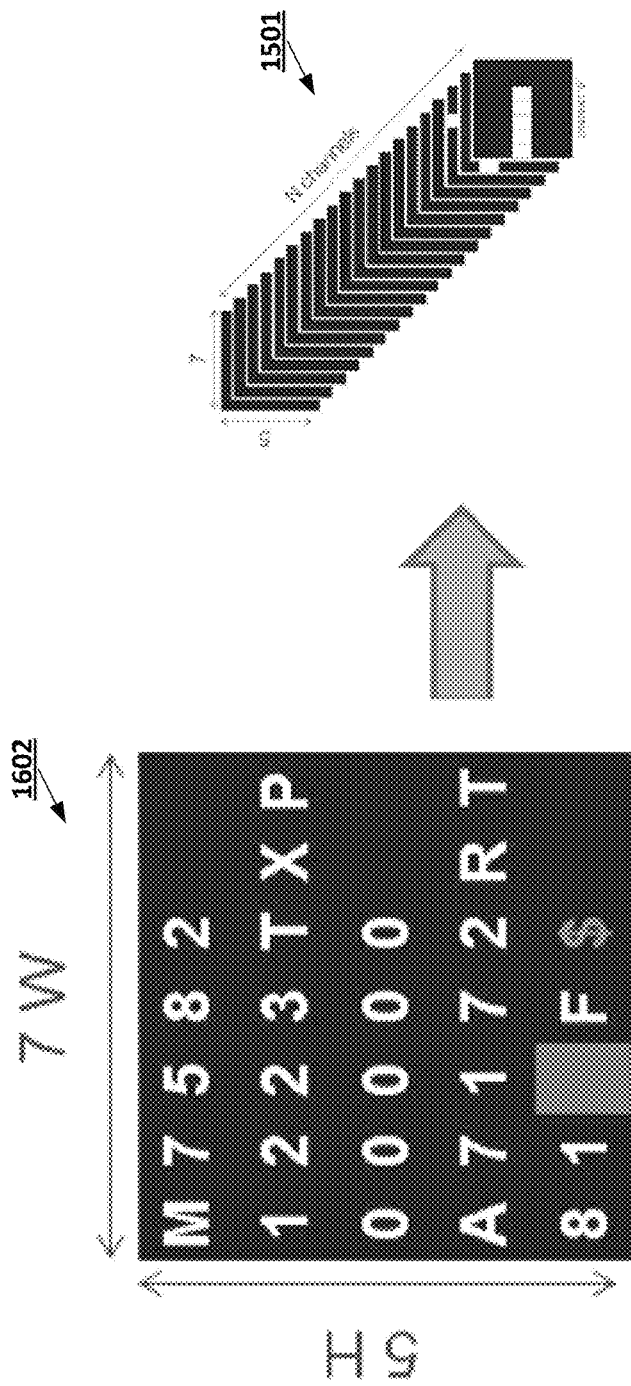

FIG. 16 provides an operational example of a dimension-size comparison between an example reserved-spatial-location image for a set of the categorical input features and a set of feature-based channels for the set of categorical input features in accordance with some embodiments discussed herein.

Figure 17:
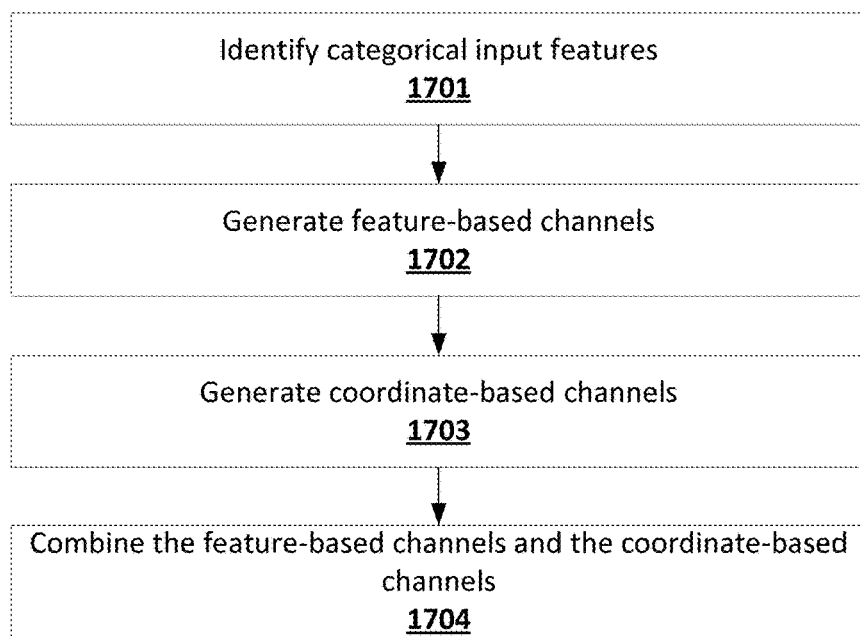

FIG. 17 is a flowchart diagram of an example process for performing feature-based and coordinate-based reservedspatial-location image transformation in accordance with some embodiments discussed herein.

Figure 18:
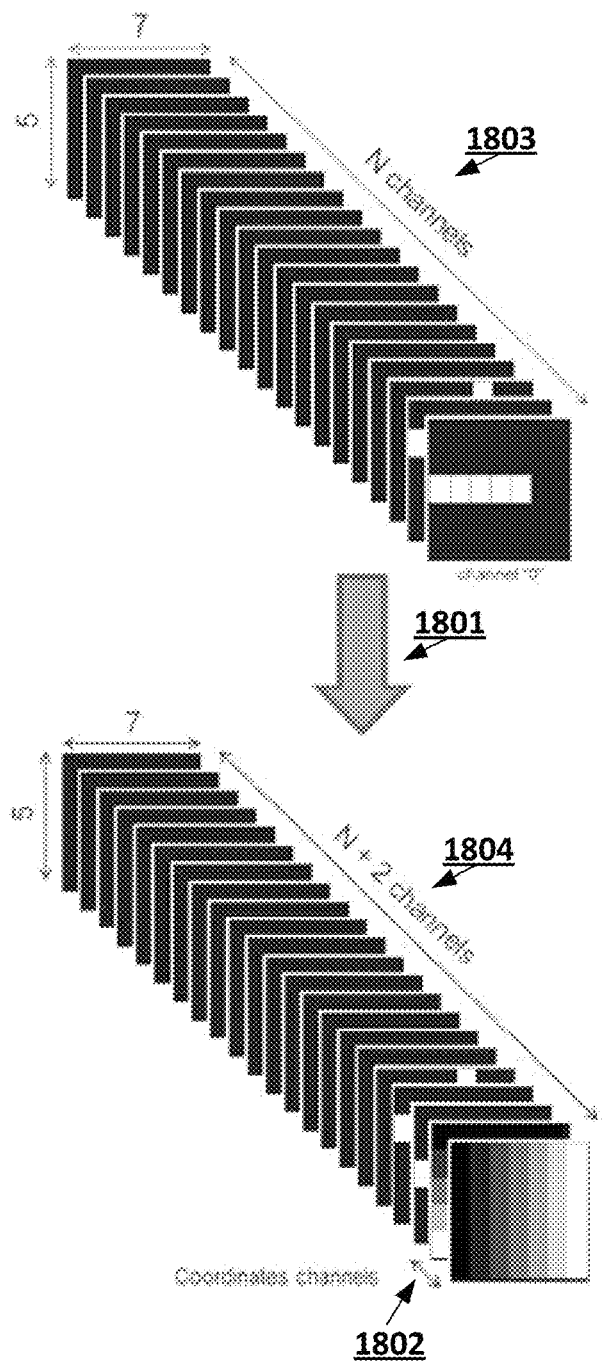

FIG. 18 provides an operational example of generating a feature-channel-based and coordinate-based reserved-spatial-location image in accordance with some embodiments discussed herein.

Figure 19:
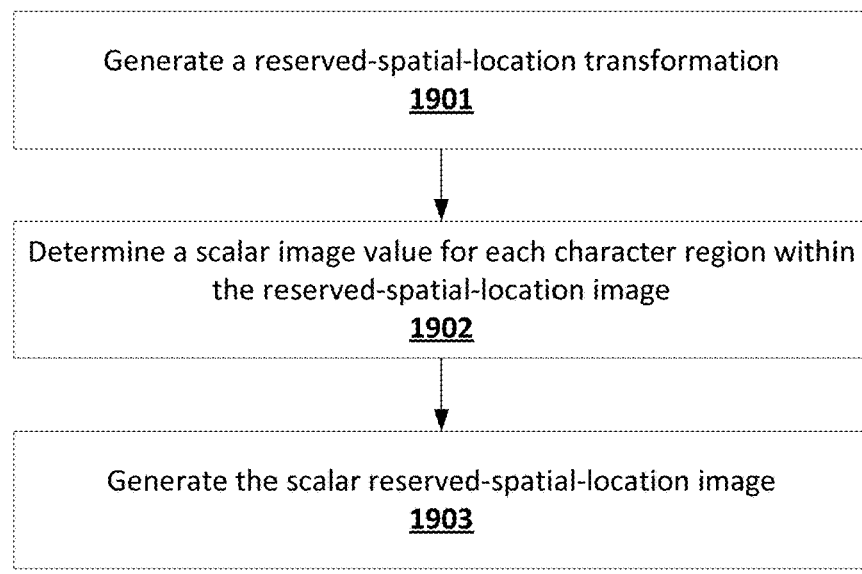

FIG. 19 is a flowchart diagram of an example process for performing scalar reserved-spatial-location image transformation in accordance with some embodiments discussed herein.

Figure 20:
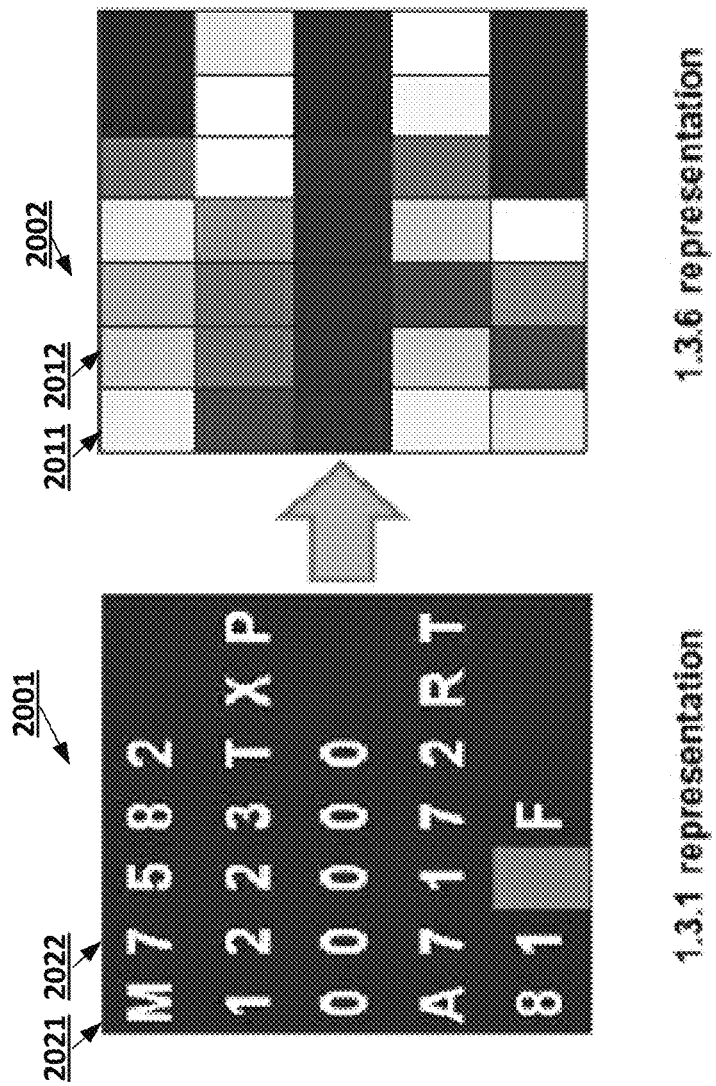

FIG. 20 provides an operational example of generating a scalar reserved-spatial-location image transformation in accordance with some embodiments discussed herein.

Figure 21:
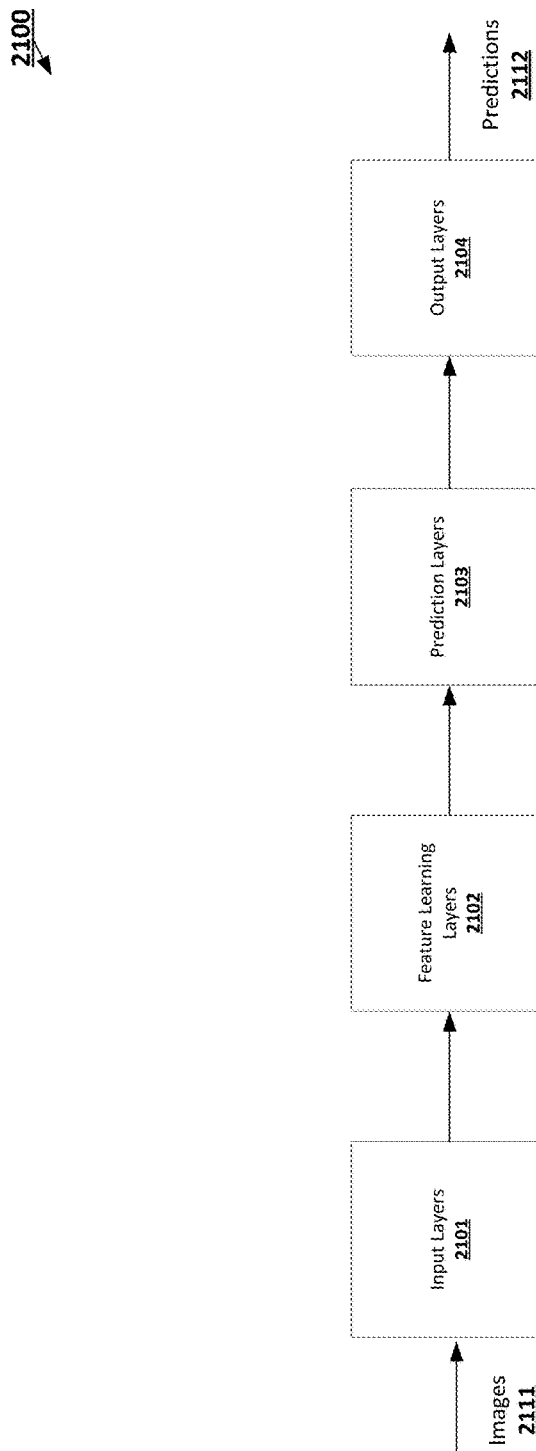

FIG. 21 is a block diagram of an example convolutional neural network architecture in accordance with some embodiments discussed herein.

Figure 22:
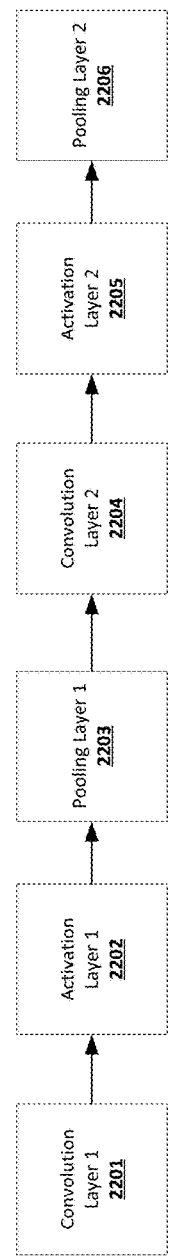

FIG. 22 is a block diagram of an example convolutional layer set architecture for a convolutional neural network in accordance with some embodiments discussed herein.

Figure 23:
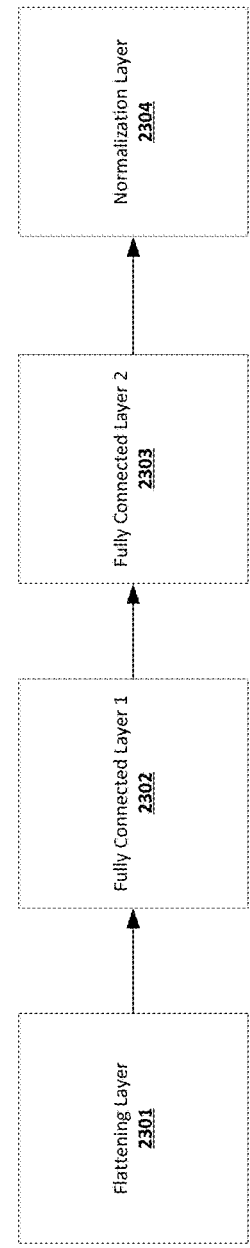

FIG. 23 is a block diagram of an example prediction layer set architecture for a convolutional neural network in accordance with some embodiments discussed herein.

Figure 24:
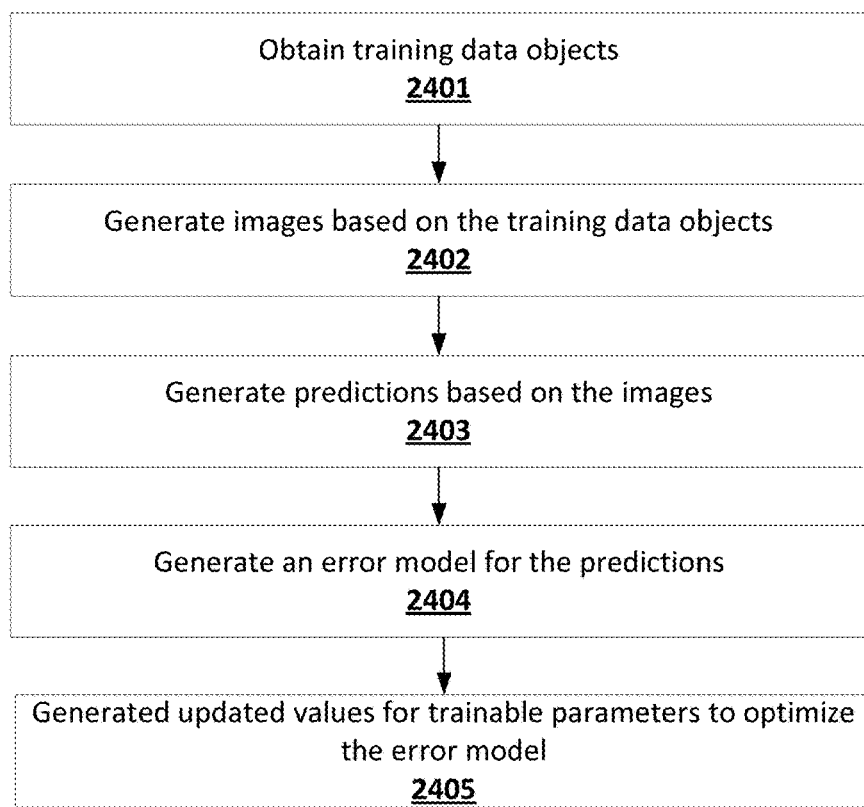

FIG. 24 is a flowchart diagram of an example process for training a machine learning model for performing image-based predictive data analysis in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Discussed herein methods, apparatus, systems, computing devices, computing entities, and/or the like for predictive data analysis of categorical data using image transformations. As will be recognized, however, the disclosed concepts can be used to perform any type of data analysis, including non-predictive data analysis. Examples of predictive data analysis include supervised machine learning analysis (e.g., classification analysis and regression analysis) and unsupervised machine learning analysis (e.g., clustering analysis). Any embodiments of the present invention described herein with reference to categorical data should be understood to refer to categorical data, scalar data, or both.

Many existing predictive data analysis solutions are incapable of efficiently and reliably performing predictive data analysis in prediction domains with complex input spaces. This is because many existing predictive data analysis solutions are developed for more common predictive data analysis tasks like image classification. For example, in the image classification domain, CNNs have accomplished tremendous success in efficiently and accurately performing predictive data analysis. Such solutions, however, are largely out of reach of developers in prediction domains with more complex input structures, such as prediction domains—with high-dimensional categorical feature spaces, prediction domains with highly sparse data, and/or prediction domains with high cardinality data. Thus, there is a technical need for predictive data analysis solutions that are capable of efficiently and reliably performing predictive data analysis in prediction domains with complex input spaces.

Various embodiments of the present invention address technical challenges related to efficiently and reliably performing predictive data analysis in prediction domains. For example, in some embodiments, proposed solutions disclose generating an image representation of one or more categorical input features, where the image representation comprises one or more image region values each associated with a categorical input feature of the one or more categorical input features, and each image region value of the one or more image region values is determined based at least in part on the corresponding categorical and/or scalar input feature associated with the image region value. After being generated, the image representation can be utilized by an image-based machine learning model (e.g., a machine learning model utilizing a CNN) to perform efficient and reliable predictive data analysis. The resulting machine learning solutions are more efficient to train and more reliable when trained.

Various embodiments of the present invention disclose various techniques for generating image representations of categorical feature data. Examples of such techniques include reserved-spatial-location image transformations and coordinate-based reserved-spatial-location image transformations. Each of those techniques generates an image representation that can be utilized to perform efficient and reliable image-based machine learning. Accordingly, by disclosing various techniques for transforming categorical/scalar feature data into image representations, various embodiments of the present invention enable utilizing efficient and reliable image-based machine learning solutions to process categorical feature data. In doing so, various embodiments of the present invention address shortcomings of existing predictive data analysis solutions and enable solutions that are capable of efficiently and reliably performing predictive data analysis in prediction domains with complex input spaces.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 provides an exemplary overview of an architecture 100 that can be used to practice embodiments of the present invention. The architecture 100 includes a predictive data analysis system 101 and one or more external computing entities 102. For example, at least some of the one or more external computing entities 102 may provide prediction inputs to the predictive data analysis system 101 and receive predictive outputs from the predictive data analysis system 101 in response to providing the prediction inputs. As another example, at least some of the external computing entities 102 may provide prediction inputs to the predictive data analysis system 101 and request performance of particular prediction-based actions in accordance with the provided predictions. As a further example, at least some of the external computing entities 102 may provide training data objects to the predictive data analysis system 101 and request the training of a predictive model in accordance with the provided training data objects. In some of the noted embodiments, the predictive data analysis system 101 may be configured to transmit parameters and/or hyper-parameters of a trained machine learning model to the external computing entities 102.

In some embodiments, the predictive data analysis computing entity 106 and the external computing entities 102 may be configured to communicate over a communication network (not shown). The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis computing entity 106 may include a predictive data analysis computing entity 106 and a storage subsystem 108. The predictive data analysis computing entity 106 may be configured to train a prediction model based at least in part on the training data 122 stored in the storage subsystem 108, store trained prediction models as part of the model definition data 121 stored in the storage subsystem 108, utilize trained models to generate predictions based at least in part on prediction inputs provided by an external computing entity 102, and perform prediction-based actions based at least in part on the generated predictions. The storage subsystem may be configured to store the model definition data 121 for one or more predictive analysis models and the training data 122 uses to train one or more predictive analysis models. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

The predictive data analysis computing entity 106 includes a feature extraction engine 111, a predictive analysis engine 112, and a training engine 113. The feature extraction engine 111 may be configured to process prediction inputs to generate relevant processed features for predictive data analysis processing by the predictive analysis engine 112. For example, the feature extraction engine 111 may be configured to generate image representations of categorical feature data (e.g., as described with reference to FIGS. 4-20). The predictive analysis engine 112 may be configured to perform predictive data analysis based at least in part on the processed features generated by the feature extraction engine 111. For example, the predictive analysis engine 112 may be configured to perform image-based predictive data analysis (e.g., by using one or more CNNs, as for example described with reference to FIGS. 21-23) based at least in part on the image representations generated by the feature extraction engine. The training engine 113 may be configured to train at least one of the feature extraction engine 111 and the predictive analysis engine 112 in accordance with the training data 122 stored in the storage subsystem 108. Example operations of the training engine 113 are described with reference to FIG. 24.

A. Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 101 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1×(1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

B. Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual- Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. Exemplary System Operations

In general, embodiments of the present invention provide methods, apparatus, systems, computing devices, computing entities, and/or the like for predictive data analysis of categorical data using image transformations. Certain embodiments utilize systems, methods, and computer program products that perform predictive analysis of categorical data using image transformations (e.g., reserved-spatial-location image transformations, coordinate-based reserved-spatial-location image transformations), and using image-based machine learning models (e.g., machine learning models that utilize CNNs).

Various embodiments of the present invention address technical challenges related to efficiently and reliably performing predictive data analysis in prediction domains. For example, in some embodiments, proposed solutions disclose generating an image representation of one or more categorical input features, where the image representation comprises one or more image region values each associated with a categorical input feature of the one or more categorical input features, and each image region value of the one or more image region values is determined based at least in part on the corresponding categorical/scalar input feature associated with the image region value. After being generated, the image representation can be utilized by an image-based machine learning model (e.g., a machine learning model utilizing a CNN) to perform efficient and reliable predictive data analysis. The resulting machine learning solutions are more efficient to train and more reliable when trained.

Image-Based Predictive Inference

FIG. 4 is a flowchart diagram of an example process 400 for performing image-based predictive data analysis. Via the various steps/operations of process 400, the predictive data analysis computing entity 106 can process categorical input features (e.g., structured text input features) to generate one or more predictive data analysis conclusions. In doing so, the predictive data analysis computing entity 106 can utilize image-based machine learning solutions (e.g., solutions utilizing CNNs) to infer important predictive insights from categorical input features, such as structured text input features.

The process 400 begins at step/operation 401 when the feature extraction engine 111 of the predictive data analysis computing entity 106 obtains one or more categorical input features. Examples of categorical input features include structured text input features, such as categorical input features that include feature data associated with a predictive entity. For example, the one or more categorical input features may include feature data (e.g., medical feature data) associated with a particular patient predictive entity. As another example, the one or more categorical input features may include feature data (e.g., transactional feature data) associated with a medical provider institution predictive entity. As yet another example, the one or more categorical input features may include feature data (e.g., word distribution feature data) associated with a medical note predictive entity.

At step/operation 402, the feature extraction engine 111 generates one or more images based at least in part on the one or more-categorical input features obtained/received in step/operation 402. In some embodiments, to generate the one or more images based at least in part on the one or more categorical input features, the feature extraction engine 111 retrieves configuration data for a particular image-based transformation routine from the model definition data 121 stored in the storage subsystem 108. Examples of image-based transformation routines are discussed below with reference to FIGS. 4-10. However, one of ordinary skill in the art will recognize that the feature extraction engine 111 may generate the one or more images by applying any suitable technique for transforming the one or more-categorical input features into the one or more images. In some embodiments, the feature extraction engine 111 selects a suitable image-based transformation routine for the one or more categorical input features given one or more properties of the categorical input features (e.g., sparseness of the one or more categorical input features, cardinality of the one or more categorical input features, size of the one or more categorical input features, structural complexity of the one or more categorical input features, accuracy of predictions generated based at least in part on the one or more categorical input features, etc.).

In some embodiments, step/operation 402 may be performed in accordance with the various steps/operations of the process depicted in FIG. 5, which is flowchart diagram of an example process for generating the one or more images by applying a reserved-spatial-location transformation to the one or more categorical/scalar input features. The process depicted in FIG. 5 begins at step/operation 501 when the feature extraction engine 111 identifies the one or more categorical/scalar input features.

At step/operation 502, the feature extraction engine 111 determines, for each categorical input feature of the one or more categorical input features, an image region within an image space. An image region within the image space is a portion of the image space defined based at least in part on two or more region dimension sizes. In some embodiments, each set of region dimension sizes for a categorical input feature of the one or more categorical input features may be defined by the transformation configuration data for the reserved-spatial-location transformation, e.g., based at least in part on one or more predefined parameters and/or one or more learned parameters determined using a training process, such as an optimization-based training process (e.g., a gradient-descent-based training process).

An operational example of a reserved-spatial-location division 600 of an image space 601 into various image regions 611-620 is depicted in FIG. 6A. As depicted in the reserved-spatial-location division 600 of FIG. 6A, image region 611 is assigned to a principal diagnosis code categorical input feature; image region 612 is assigned to a provider taxonomy categorical input feature; image region 613 is assigned to a provider state categorical input feature; image region 614 is assigned to a par/non-par designation categorical input feature; image region 615 is assigned to a procedure code categorical input feature; image region 616 is assigned to a modifier code input feature; image region 617 is assigned to a place of service code categorical input feature; image region 618 is assigned to a provider-patient distance scalar input feature; image region 619 is assigned to a patient-gender-and-age categorical and scalar input features; and image region 620 is assigned to a claim amount scaler input feature.

At step/operation 503, the feature extraction engine 111 determines, for each image region determined in step/operation 502, an image region value based at least in part on the categorical input feature that is associated with the particular image region. In some embodiments, the image region value for a particular image region includes pixel values for the particular image region.

At step/operation 504, the feature extraction engine 111 generates a reserved-spatial-location image based at least in part on each image region value determined in step/operation 503. In some embodiments, the feature extraction engine 111 combines each image region value in a corresponding image region for the image region value in order to generate the reserved-spatial-location image based at least in part on each image region value determined in step/operation 503.

An operational example of a reserved-spatial location image 700 is depicted in FIG. 7. As depicted in reserved-spatial location image 700, each image region 711-720 is associated with a particular image region value. For example, the image region 711 (associated with a principal diagnosis code categorical input feature) has a corresponding image region value that depicts the text value "M7582"; the image region 712 (associated with a level 2 provider specialization code categorical input feature) has a corresponding image region value that depicts the text value "1223"; the image region 713 (associated with a provider state code categorical input feature) has a corresponding image region value that depicts the text value "TX"; the image region 714 (associated with a participant provider identifier categorical input feature) has a corresponding image region value that depicts the text value "P"; the image region 715 (associated with a level 3 provider specialization code categorical input feature) has a corresponding image region value that depicts the text value "00000"; the image region 716 (associated with a procedure code categorical input feature) has a corresponding image region value that depicts the text value "A7172"; the image region 717 (associated with a modifier code categorical input feature) has a corresponding image region value that depicts the text value "RT"; the image region 718 (associated with a place-of-service code categorical input feature) has a corresponding image region value that depicts the text value "81"; the image region 719 (associated with a provider-patient distance scalar input feature) has a corresponding image region value that depicts the value 1161; and the image region 720 (associated with a claim amount scalar input feature) has a corresponding image region value whose color intensity depicts the value 1000.

In some embodiments, step/operation 402 may be performed in accordance with the various steps/operations of process depicted in FIG. 8, which is a flowchart diagram of an example process for generating one or more images by applying a coordinate-based reserved-spatial-location transformation based at least in part on one or more categorical input features. The process depicted in FIG. 8 begins at step/operation 801 when the feature extraction engine 111 identifies the one or more categorical input features.

At step/operation 802, the feature extraction engine 111 identifies coordinate channels associated an image space. In some embodiments, the coordinate channels are determined based at least in part on foundational coordinates associated with the feature data. For example, if the image space is associated with an RGB (red-green-blue) image, the plurality of coordinate channels may include a red channel, a green channel, and a blue channel.

At step/operation 803, the feature extraction engine 111 assigns each categorical input feature obtained/received in step/operation 801 to a coordinate grouping of a plurality of coordinate groupings. For example, the feature extraction engine 111 may assign a first group of categorical input features that relate to medical claim identifying information into a first coordinate grouping; a second group of categorical input features that relate to predictive entity identifying information into a second coordinate grouping; and a third remaining group of categorical input features into a third coordinate grouping. In some embodiments, the number of the coordinate groupings and/or the assignment of the categorical input features to the coordinate groupings may be defined by the transformation configuration data for the coordinate-based reserved-spatial-location transformation, e.g., based at least in part on one or more predefined parameters and/or one or more learned parameters determined using a training process, such as an optimization-based training process (e.g., a gradient-descent-based training process).

In some embodiments, the feature extraction engine 111 divides the categorical input features into the plurality of coordinate groupings in a matter that minimizes the likelihood that similar values and/or values having similar formats will belong to the same coordinate grouping. For example, if two categorical input features may both take the value "TX," the feature extraction engine 111 may assign the two categorical input features to different coordinate groupings. As another example, the feature extraction engine 111 may assign various categorical input features configured to different coordinate groupings, various scalar input features configured to have intensity values-to different coordinate groupings, etc.

At step/operation 804, the feature extraction engine 111 assigns each coordinate grouping generated in step/operation 803 to a coordinate channel identified in step/operation 802. For example, the feature extraction engine 111 may assign a red color-based channel in an RGB image space to claim-information, a green color-based channel in the RGB image space to a horizontal coordinate, and a blue color-based channel in the RGB image space to a vertical coordinate. In some embodiments, the assignment of coordinate groupings to coordinate channels may be defined by the transformation configuration data for the coordinate-based reserved-spatial-location transformation, e.g., based at least in part on one or more predefined parameters and/or one or more learned parameters determined using a training process, such as an optimization-based training process (e.g., a gradient-descent-based training process).

At step/operation 805, the feature extraction engine 111 generates the coordinate-based reserved-spatial location image based on each coordinate channel. Operational examples are depicted in FIGS. 9A-9C. In particular, the green channel 910 depicts an example of a possible horizontal coordinates; the blue channel 940 depicts an example of a possible vertical coordinates; and claim information.

An operational example of generating a coordinate-based reserved-spatial-location 1010 based at least in part on coordinates and information channels 1001-1003 as depicted in FIG. 10. As depicted in FIG. 10, the green channel 1001 (associated with horizontal coordinates) is merged with the blue channel 1002 (associated with vertical coordinates) to generate a coordinate system 1003. Then, the coordinate system 1003 is merged with the red channel 1004 (associated with information channel) to generate the coordinate-based reserved-spatial-location image representation 1005.

In some embodiments, step/operation 402 may be performed in accordance with the various steps/operations of FIG. 1100, which is a flowchart diagram of an example process for generating one or more images by applying a reserved-pattern transformation to one or more categorical input features. The process depicted in FIG. 11 begins at step/operation 1101 when the feature extraction engine 111 identifies the one or more categorical input features At step/operation 1102, the feature extraction engine 111 assigns a formatting pattern to each categorical input feature obtained/received in step/operation 1101. A formatting pattern may indicate a range of characters (e.g., ASCII characters and/or Unicode characters) that can be used to represent values associated with the categorical input feature. Examples of formatting patterns include an English alphanumeric range of characters, an Arabic alphanumeric range of characters, a range of characters including {K, 1, 3, $, #}, etc.

At step/operation 1103, the feature extraction engine 111 determines, for each identified image region, an image region value based at least in part on the categorical input feature that is associated with the particular image region and the formatting pattern for the categorical input feature. In some embodiments, the image region value for a particular image region includes pixel values for the particular image region.

At step/operation 1104, the feature extraction engine 111 generates a reserved-pattern image based at least in part on each image region value determined in step/operation 1104. In some embodiments, the feature extraction engine 111 combines each image region value in a corresponding image region for the image region value to generate the reserved-pattern image based at least in part on each image region value determined in step/operation 1104.

An operational example of a reserved-pattern image 1200 is depicted in FIG. 12. As depicted in the reserved-pattern image 1200, each image region 1211-1221 is associated with an image region value. For example, the image region 1211 (associated with a principal diagnosis code categorical input feature) has a corresponding image region value associated with a first formatting pattern; the image region 1212 (associated with a level 2 provider taxonomy code categorical input feature) has a corresponding image region value associated with a second formatting pattern; the image region 1213 (associated with a provider state code categorical input feature) has a corresponding image region value associated with a third formatting pattern; the image region 1214 (associated with a participant provider identifier categorical input feature) has a corresponding image region value associated with a fourth formatting pattern; the image region 1215 (associated with a level 3 provider taxonomy code categorical input feature) has a corresponding image region value associated with a fifth formatting pattern; the image region 1216 (associated with a procedure code categorical input feature) has a corresponding image region value associated with a sixth formatting pattern; the image region 1217 (associated with a modifier code categorical input feature) has a corresponding image region value associated with a seventh formatting pattern; the image region 1218 (associated with a place-of-service code categorical input feature) has a corresponding image region value associated with an eight formatting pattern; the image region 1219 (associated with a provider-patient distance scalar input feature) has a corresponding image region value associated with a ninth formatting pattern; the image region 1220 (associated with a patient-gender-and-age categorical and scalar input features) has a corresponding image region value associated with a tenth formatting pattern; and the image region 1221 (associated with a claim amount categorical input feature) has a corresponding image region associated with an eleventh formatting pattern.

In some embodiments, step/operation 402 may be performed in accordance with the various steps/operations of FIG. 13, which is a flowchart diagram of an example process for generating one or more images by applying a feature-channel-based reserved-spatial-location transformation to the one or more categorical input features. The process depicted in FIG. 13 begins at step/operation 1301 when the feature extraction engine 111 obtains/receives the one or more categorical input features. At step/operation 1302, the feature extraction engine 111 determines one or more character patterns for each of the one or more categorical input features, where each character pattern is associated with an ordered combination of one or more alphanumeric characters.

At step/operation 1303, the feature extraction engine 111 determines, for each categorical input feature of the one or more categorical input features, an image region within an image space. An image region within the image space is a portion of the image space defined based at least in part on two or more region dimension sizes. For example, an image region within an image space may include one pixel of the image space. In some embodiments, because feature-channel-based reserved-spatial-location transformation utilizes various feature-based channels each corresponding to the image space, the image space size for the image space utilized for feature-channel-based reserved-spatial-location transformation may be smaller than the image space size for the image space utilized for reserved-spatial-location transformation, coordinate-based reserved-spatial-location transformation, and/or reserved-pattern transformation.

At step/operation 1304, the feature extraction engine 111 generates a feature-based channel for each character pattern, where the feature-based channel for a particular character pattern indicates whether various categorical features include the particular character pattern. Operational examples of feature-based channels are depicted in the feature-based channels 1401-1406 of FIGS. 14A-F correspondingly. In each of the feature-based channels 1401-1406, each pixel corresponds to the image region for a particular categorical input feature. Accordingly, a white value for an image region within a particular feature-based channel 1401-1406 indicates presence of the character pattern associated with the feature-based channel 1401-1406 in the categorical input feature associated with the image region, while a black value for an image region within a particular feature-based channel 1401-1406 indicates absence of character pattern associated with the feature-based channel 1401-1406 in the categorical input feature associated with the image region.

For example, with respect to the feature-based channel 1401 of FIG. 14A which is associated with presence of the character "0" in various categorical input features, the white value of pixel 1411 indicates presence of the character "0" in a categorical input feature associated with the pixel 1411. With respect to the feature-based channel 1402 of FIG. 14B which is associated with presence of the character "1" in various categorical input features, the black value of pixel 1412 indicates absence of the character "1" in a categorical input feature associated with the pixel 1412. With respect to the feature-based channel 1403 of FIG. 14C which is associated with presence of the character "2" in various categorical input features, the white value of pixel 1413 indicates presence of the character "2" in a categorical input feature associated with the pixel 1413. With respect to the feature-based channel 1404 of FIG. 14D which is associated with presence of the character "A" in various categorical input features, the black value of pixel 1414 indicates absence of the character "A" in a categorical input feature associated with the pixel 1414. With respect to the feature-based channel 1405 of FIG. 14E which is associated with presence of the character "T" in various categorical input features, the white value of pixel 1415 indicates presence of the character "T" in a categorical input feature associated with the pixel 1415. With respect to the feature-based channel 1406 of FIG. 14F which is associated with presence of the character "Z" in various categorical input features, the black value of pixel 1416 indicates absence of the character "Z" in a categorical input feature associated with the pixel 1416.

In some embodiments, the feature extraction engine 111 combines the feature-based channels generated in step/operation 1304 to generate the one or more images corresponding to a feature-channel-based reserved-spatial-location transformation of the one or more categorical input features. An operational example of a set of combined feature-based channels 1501 is depicted in FIGS. 15-16.

In some embodiments, step/operation 402 may be performed in accordance with the various steps/operations of FIG. 17, which is a flowchart diagram of an example process for generating one or more images based at least in part on a feature-channel-based and coordinate-based reserved-spatial-location transformation of one or more categorical input features. The process depicted in FIG. 17 begins at step/ operation 1701 when the feature extraction engine 111 identifies the one or more categorical input features. At step/operation 1702, the feature extraction engine 111 generates one or more feature-based channels for the one or more categorical input features (e.g., by using the process depicted in FIG. 13). At step/operation 1703, the feature extraction engine 111 generates one or more coordinate channels for the one or more categorical input features (e.g., by using the process depicted in FIG. 8).

At step/operation 1704, the feature extraction engine 111 combines the one or more feature-based channels generated in step/operation 1702 and the one or more coordinate channels generated in step/operation 1703 to generate the feature-channel-based and coordinate-based reserved-spatial-location transformation of one or more categorical input features. An operational example of generating a feature-channel-based and coordinate-based reserved-spatial-location transformation 1801 is depicted in FIG. 18, which depicts merging two coordinate channels 1802 with N feature-based channels 1803 in order to generate the feature-channel-based and coordinate-based reserved-spatial-location transformation 1804 for one or more categorical input features.

In some embodiments, step/operation 402 may be performed in accordance with the various steps/operations of FIG. 19, which is a flowchart diagram of an example process for generating one or more images based at least in part on a scalar reserved-spatial-location transformation of one or more categorical input features. The process depicted in FIG. 19 begins at step/operation 1901 when the feature extraction engine 111 generates a reserved-spatial-location image of the one or more categorical input features. At step/operation 1902, the feature extraction engine 111 determines a corresponding scalar image value for each character region within the reserved-spatial-location image of the one or more categorical input features. For example, the feature extraction engine 111 may determine a grayscale value for each portion of the reserved-spatial-location image that corresponds to a particular character based at least in part on a mapping of characters to grayscale values. At step/operation 1903, the feature extraction engine 111 generates the scalar reserved-spatial-location image of the one or more categorical input features based at least in part on each scalar value determined in step/operation 1902.

An operational example of a scalar reserved-spatial-location image 2002 is depicted in FIG. 20. The scalar image value of each character region (e.g., character regions 2011 and 2012) in the scalar reserved-spatial-location image 2002 is determined based at least in part on a value of a character associated with the particular character region. For example, as depicted in FIG. 20, the scalar image value of character region 2011 in the scalar reserved-spatial-location image 2002 is determined based at least in part on the value of the character "M" 2021 from the reserved-spatial location image 2001, while the scalar image value of character region 2012 in the scalar reserved-spatial-location image 2001 is determined based at least in part on the value of the character "7" 2122 from the reserved-spatial location image 2001. In some embodiments, the feature extraction engine 111 may map character values associated with the characters "M" and "7" (e.g., ASCII or Unicode character values associated with the two noted characters) to grayscale values.

At step/operation 403, the predictive analysis engine 112 processes the one or images using an image-based machine learning model to generate one or more predictions. Examples of an image-based machine learning models include a machine learning model that utilizes a CNN. Other examples of an image-based machine learning model include a feedforward neural network. In some embodiments, the image-based machine learning model may utilize a CNN in coordination with one or more other machine learning models.

In some embodiments, step/operation 403 may be performed in accordance with the convolutional neural network architecture 2100 depicted in the block diagram of FIG. 21. As depicted in FIG. 21, the predictive analysis engine 112 receives one or more images 2111 generated by the feature extraction engine 111 using one or more input layers 2101. As further depicted in FIG. 21, the predictive analysis engine 112 utilizes one or more feature learning layers 2102 to process the output of the one or more input layers 2101 to generate one or more convolutional layer outputs. In some embodiments, the one or more feature learning layers 2102 are configured to perform a combination of one or more successive feature learning routines, where each feature learning routine of the one or more successive feature routines includes performing a convolutional operation (e.g., a convolutional operation using one or more kernels and/or one or more filters) followed by an activation operation (e.g., a rectified linear unit (ReLU) activation operation) and followed by a pooling operation (e.g., a non-linear down-sampling operation, such as a max pool operation). For example, as depicted in the block diagram of FIG. 22, the one or more feature learning layers 2102 may include two successive feature learning routines, i.e., a first convolutional operation performed by a first convolutional layer 2201, followed by a first activation operation by a first activation layer 2202, followed by a first pooling operation by a first pooling layer 2203, followed by a second convolutional operation by a second convolutional layer 2204, followed by a second activation operation by a second activation layer 2205, and followed by a second pooling operation by a second pooling layer 2206.

As further depicted in FIG. 21, the predictive analysis engine 112 utilizes one or more prediction layers 2103 to process the one or more convolutional layer outputs generated by the one or more feature learning layers 2102 to generate one or more raw prediction outputs. In some embodiments, the one or more prediction layers 2103 including one or more fully connected neural network layers. For example, as depicted in the block diagram of FIG. 24, the one or more prediction layers 2103 may include a flattening layer 2301 configured to generate a flattened version of the one or more convolutional layer outputs generated by the one or more feature learning layers 2102, two fully connected layers 2302-2303, and a normalization layer 2304 (e.g., a softmax normalization layer). Moreover, the predictive analysis engine 112 utilizes one or more output layers 2104 to generate one or more predictions 2112 based at least in part on the raw prediction outputs generated by the one or more prediction layers 2103.

At step/operation 404, the predictive analysis engine 112 performs a prediction-based actions based at least in part on the predictions generated in step/operation 403. Examples of prediction-based actions include transmission of communications, activation of alerts, automatic scheduling of appointments, etc. As a further example, the predictive analysis engine 112 may determine based at least in part on operational data associated with one or more medical institutions that the one or more medical institutions exhibit patterns of wasteful and/or fraudulent insurance claim filings.

Training Image-Based Prediction Models

FIG. 24 is a flowchart diagram of an example process 2400 for training a machine learning model for performing image-based predictive data analysis. Via the various steps/operations of the process 2400, the predictive data analysis computing entity 106 can train a machine learning model to process categorical/scalar input features (e.g., structured text input features) to generate one or more predictive data analysis conclusions.

The process 2400 begins at step/operation 2401 when the feature extraction engine 111 obtains/receives one or more training data objects, where each training data object includes one or more categorical/scalar training input features and one or more ground-truth determinations for the one or more categorical/scalar input features. For example, the one or more training categorical/scalar input features in a particular training data object may include one or more patient features for a patient, while the one or more ground-truth determinations in the particular training data object may include particular health information (e.g., particular diagnostic information) associated with the patient predictive entity. As another example, the one or more training-categorical/scalar input features in a particular training data object may include one or more operational features for a medical provider predictive entity, while the one or more ground-truth determinations in the particular training data object may include particular operational information (e.g., particular operational statistics) associated with the medical predictive entity. The feature extraction engine 111 may retrieve the categorical/scalar input features from the training data 122 stored on the storage subsystem and/or receive the categorical/scalar input features from the training data 122 from one or more external computing entities 102.

At step/operation 2402, the feature extraction engine 111 generates one or more images based at least in part on the one or more training data objects obtained/received in step/operation 2401. For example, the feature extraction engine 111 may process the one or more categorical/scalar training input features associated with the training data objects (e.g., in accordance with a process substantially similar to the process 400 of FIG. 4) to generate one or more images based at least in part on the one or more training data objects obtained/received in step/operation 2401. In some embodiments, the feature extraction engine 111 provides the generated one or more images to the predictive analysis engine 112.

At step/operation 2403, the predictive analysis engine 112 generates one or more predictions based at least in part on the one or more images generated in step/operation 2404. For example, the predictive analysis engine 112 may process the one or more images generated by the predictive analysis engine 112 (e.g., using a CNN, such as the CNN 2100 of FIG. 21) to generate one or more predictions based at least in part on the one or more images generated by the feature extraction engine 111 in step/operation 2404. In some embodiments, the predictive analysis engine 112 provides the generated one or more predictions to the training engine 113.

At step/operation 2404, the training engine 113 generates an error model based at least in part on the one or more predictions. In some embodiments, the training engine 113 generates a measure of deviation between each of the one or more predictions and a corresponding ground-truth determination in a training data object associated with the particular prediction. The training engine 113 may then compute an overall error measure based at least in part on the measure of deviation. The training engine 113 may then generate the error model as a model that relates the overall error measure to one or more trainable parameters of the machine learning model (e.g., at least one of one or more trainable parameters associated with the feature extraction engine 111 and one or more trainable parameters associated with the predictive analysis engine 112).

At step/operation 2405, the training engine 113 generates updated values for one or more trainable parameters of the machine learning model in a manner that achieves an optimization of the error model. In some embodiments, the training engine 113 may generate the updated values for the one or more trainable parameters of the machine learning model in a manner that achieves a local optimization of the error model. In some embodiments, the training engine 113 may generate the updated values for the one or more trainable parameters of the machine learning model in a manner that achieves a global optimization of the error model. In some embodiments, to generate the updated values for the one or more trainable parameters of the machine learning model in a manner that achieves an optimization of the error model, the training engine 113 uses one or more training algorithms, such as a gradient-descent-based training algorithm.

Although the techniques described herein for generating image representations of categorical/scalar feature data are explained with reference to performing predictive data analysis, a person of ordinary skill in the relevant technology will recognize that the disclosed techniques have applications far beyond performing predictive data analysis. As an illustrative example, the disclosed techniques can be used in various data visualization applications. As another illustrative example, the disclosed techniques can be used to encode data in image-based data structures that facilitate at least one of data retrieval and data security. As yet another example, the disclosed techniques can be utilized to enhance various steganography techniques. As a further illustrative example, the disclosed techniques can be used to process and store data in spatial-temporal databases. In some embodiments, the disclosed techniques can be used to generate video representations of categorical/scalar feature data, e.g., video representations that illustrate changes in the corresponding categorical/scalar feature over time.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating an image representation of a plurality of categorical input features for a plurality of categorical input feature types, the computer-implemented method comprising:
  determining a plurality of image region values, wherein:
    (i) each image region value is associated with a respective image region of a plurality of image regions, (ii) each image region is associated with a respective categorical input feature type of the plurality of categorical input feature types, and (iii) each image region value is determined in a manner such that the respective image region for the image region value displays a visual representation of textual data associated with a respective categorical input feature for the respective categorical input feature type that is associated with the respective image region for the image region value; and generating the image representation based at least in part on the plurality of image region values.

2. The computer-implemented method of claim 1, wherein:

each categorical input feature type of the plurality of categorical input feature types is associated with a text formatting pattern, and the textual data associated with at least one image region value of plurality of image region values is determined based at least in part on the text formatting pattern for the categorical input feature type that is associated with the image region value.

3. The computer-implemented method of claim 1, wherein generating the image representation further comprises:

generating a raw image representation of the plurality of categorical input features, wherein (i) the raw image representation is associated with a plurality of raw image region values, (ii) each raw image region value is associated with a categorical input feature type of the plurality of categorical input features, (iii) each raw image region value of the plurality of raw image region values is determined based at least in part on the corresponding categorical input feature associated with the raw image region value, (iv) at least one raw image region value of the plurality of image region values is configured to depict a visual representation of textual data associated with the categorical input feature that is associated with the raw image region value;

determining, based at least in part on the raw image representation, a plurality of character regions within the raw image representation, wherein each character region depicts a portion of the visual representation that corresponds to a corresponding character of a plurality of characters of the textual data;

determining, for each character region of the plurality of character regions, a character region scalar value and a character region location within the raw image representation; and generating the image representation to comprise, for each character region of the plurality of character regions, a scalar visual representation of the character region scalar value for the character region in the character region location for the character region.

4. The computer-implemented method of claim 1, further comprising processing the image representation using an image-based machine learning model to generate an image-based prediction.

5. The computer-implemented method of claim 4, wherein:

the plurality of categorical input features comprise one or more patient features associated with a patient, and the image-based prediction is a health prediction for the patient.

6. The computer-implemented method of claim 1, wherein the computer-implemented method is performed in response to selecting a first image generation technique of a plurality of image generation techniques.

7. The computer-implemented method of claim 6, wherein:

the plurality of image generation techniques comprise a second image generation technique, and the second image generation technique comprises:

determining, for each categorical input feature, a corresponding coordinate grouping of a plurality of coordinate groupings; and generating, for each coordinate grouping of the plurality of coordinate groupings, a coordinate channel; and determining the image representation based at least in part on each coordinate channel.

8. The computer-implemented method of claim 6, wherein:

the plurality of image generation techniques comprise a third image generation technique, and the third image generation technique comprises:

identifying a plurality of character patterns;

generating, for each character pattern of a plurality of character pattern, a feature-based channel of a plurality of feature-based channels, wherein: (i) each feature-based channel comprises one or more feature-based channel region values, and (ii) each feature-based channel region value for a corresponding feature-based channel is associated with a corresponding categorical input feature, and (iii) each feature-based channel region value for a corresponding feature-based channel is determined based at least in part on whether the corresponding categorical input feature for the feature-based channel region value comprises the corresponding character pattern associated with the corresponding feature-based channel; and generating the image representation based at least in part on each corresponding feature-based channel of the plurality of feature-based channels.

9. An apparatus for generating an image representation of on a plurality of categorical input features for a plurality of categorical input feature types, the apparatus comprising at least one processor and at least one memory including a computer program code, the at least one memory and the computer program code configured to, with the at least one processor, cause the apparatus to:

determine a plurality of image region values, wherein: (i) each image region value is associated with a respective image region of a plurality of image regions, (ii) each image region is associated with a respective categorical input feature type of the plurality of categorical input feature types, and (iii) each image region value is determined in a manner such that the respective image region for the image region value displays a visual representation of textual data associated with a respective categorical input feature for the respective categorical input feature type that is associated with the respective image region for the image region value; and generate the image representation based at least in part on the plurality of image region values.

10. The apparatus of claim 9, wherein:

each categorical input feature type of the plurality of categorical input feature types is associated with a text formatting pattern, and the textual data associated with at least one image region value of the plurality of image region values is determined based at least in part on the text formatting pattern for the categorical input feature type that is associated with the image region value.

11. The apparatus of claim 9, wherein generating the image representation further comprises:

generating a raw image representation of the plurality of categorical input features, wherein (i) the raw image representation is associated with a plurality of raw image region values, (ii) each raw image value is associated with a categorical input feature of the plurality of categorical input features, (iii) each raw image region value of the plurality of raw image region values is determined based at least in part on the corresponding categorical input feature associated with the raw image region value, (iv) at least one raw image region value of the plurality of image region values is configured to depict a visual representation of textual data associated with the categorical input feature that is associated with the raw image region value;

determining, based at least in part on the raw image representation, a plurality of character regions within the raw image representation, wherein each character region depicts a portion of the visual representation that corresponds to a corresponding character of a plurality of characters of the textual data;

determining, for each character region of the plurality of character regions, a character region scalar value and a character region location within the raw image representation; and generating the image representation to comprise, for each character region of the plurality of character regions, a scalar visual representation of the character region scalar value for the character region in the character region location for the character region.

12. The apparatus of claim 9, further comprising processing the image representation using an image-based machine learning model to generate an image-based prediction.

13. The apparatus of claim 12, wherein:
the plurality of categorical input features comprise one or more patient features associated with a patient, and
the image-based prediction is a health prediction for the patient.

14. The apparatus of claim 9, wherein the computer-implemented method is performed in response to selecting a first image generation technique of a plurality of image generation techniques.

15. The apparatus of claim 14, wherein:
the plurality of image generation techniques comprise a second image generation technique, and
the second image generation technique comprises:
determining, for each categorical input feature, a corresponding coordinate grouping of a plurality of coordinate groupings; and
generating, for each coordinate grouping of the plurality of coordinate groupings, a coordinate channel; and
determining the image representation based at least in part on each coordinate channel.

16. The apparatus of claim 14, wherein:
the plurality of image generation techniques comprise a third image generation technique, and
the third image generation technique comprises:
identifying a plurality of character patterns;
generating, for each character pattern of a plurality of character pattern, a feature-based channel of a plurality of feature-based channels, wherein: (i) each feature-based channel comprises one or more feature-based channel region values, and (ii) each feature-based channel region value for a corresponding feature-based channel is associated with a corresponding categorical input feature, and (iii) each feature-based channel region value for a corresponding feature-based channel is determined based at least in part on whether the corresponding categorical input feature for the feature-based channel region value comprises the corresponding character pattern associated with the corresponding feature-based channel; and
generating the image representation based at least in part on each corresponding feature-based channel of the plurality of feature-based channels.

17. A non-transitory computer storage medium comprising instructions for generating an image representation of on plurality of categorical input features for a plurality of categorical input feature types, the instructions being configured to cause one or more processors to at least perform operations configured to:

determine a plurality of image region values, wherein: (i) each image region value is associated with a respective image region of a plurality of image regions, (ii) each image region is associated with a respective categorical input feature type of the plurality of categorical input feature types, and (iii) each image region value is determined in a manner such that the respective image region for the image region value displays a visual representation of textual data associated with a respective categorical input feature for the respective categorical input feature type that is associated with the respective image region for the image region value; and generate the image representation based at least in part on the plurality of image region values.

18. The non-transitory computer storage medium of claim 17, wherein:
each categorical input feature type of the plurality of categorical input features is associated with a text formatting pattern, and
the textual data associated with at least one image region value of the plurality of image region values is determined based at least in part on the text formatting pattern for the categorical input feature type that is associated with the image region value.

19. The non-transitory computer storage medium of claim 17, wherein generating the image representation further comprises:
generating a raw image representation of the plurality of categorical input features, wherein (i) the raw image representation is associated with a plurality of raw image region values, (ii) each raw image value is associated with a categorical input feature of the plurality of categorical input features, (iii) each raw image region value of the plurality of raw image region values is determined based at least in part on the corresponding categorical input feature associated with the raw image region value, (iv) at least one raw image region value of the plurality of image region values is configured to depict a visual representation of textual data associated with the categorical input feature that is associated with the raw image region value;

determining, based at least in part on the raw image representation a plurality of character regions within the raw image representation, wherein each character region depicts a portion of the visual representation that corresponds to a corresponding character of a plurality of characters of the textual data;

determining, for each character region of the plurality of character regions, a character region scalar value and a character region location within the raw image representation; and generating the image representation to comprise, for each character region of the plurality of character regions, a scalar visual representation of the character region scalar value for the character region in the character region location for the character region.

20. The non-transitory computer storage medium of claim 17, further comprising processing the image representation using an image-based machine learning model to generate an image-based prediction.

* * * * *